United States Patent
Ohno et al.

(10) Patent No.: US 9,848,782 B2
(45) Date of Patent: Dec. 26, 2017

(54) BLOOD PRESSURE ESTIMATION DEVICE, BLOOD PRESSURE ESTIMATION METHOD, BLOOD PRESSURE MEASUREMENT DEVICE, AND RECORDING MEDIUM

(71) Applicant: NEC CORPORATION, Tokyo (JP)

(72) Inventors: Yuji Ohno, Tokyo (JP); Masahiro Kubo, Tokyo (JP); Kimiyasu Takoh, Tokyo (JP); Katsumi Abe, Tokyo (JP); Ersin Altintas, Tokyo (JP); Hiroshi Imai, Tokyo (JP); Osamu Tochikubo, Kanagawa (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 15/118,267

(22) PCT Filed: Feb. 13, 2015

(86) PCT No.: PCT/JP2015/000667
§ 371 (c)(1),
(2) Date: Aug. 11, 2016

(87) PCT Pub. No.: WO2015/122191
PCT Pub. Date: Aug. 20, 2015

(65) Prior Publication Data
US 2016/0360982 A1 Dec. 15, 2016

(30) Foreign Application Priority Data
Feb. 13, 2014 (JP) .................. 2014-025371

(51) Int. Cl.
*A61B 6/00* (2006.01)
*A61B 5/022* (2006.01)
(Continued)

(52) U.S. Cl.
CPC ........ *A61B 5/02225* (2013.01); *A61B 5/7207* (2013.01); *A61B 5/7278* (2013.01);
(Continued)

(58) Field of Classification Search
CPC . A61B 5/02225; A61B 5/7207; A61B 5/7278; A61B 5/02116
See application file for complete search history.

(56) References Cited

U.S. PATENT DOCUMENTS

| | | | |
|---|---|---|---|
| 2002/0099298 A1* | 7/2002 | Yokozeki | A61B 5/022 600/494 |
| 2004/0024325 A1 | 2/2004 | Nishibayashi et al. | |
| 2013/0071129 A1 | 3/2013 | Yoneda et al. | |

FOREIGN PATENT DOCUMENTS

| | | |
|---|---|---|
| CN | 1936638 A | 3/2007 |
| CN | 102124387 A | 7/2011 |

(Continued)

OTHER PUBLICATIONS

International Search Report for PCT/JP2015/000667 dated Apr. 21, 2015.
(Continued)

*Primary Examiner* — Robert N Wieland
(74) *Attorney, Agent, or Firm* — Sughrue Mion, PLLC

(57) ABSTRACT

Provided are a blood pressure estimation device, and the like, the device being capable of accurately estimating blood pressure. The blood pressure estimation device includes a blood pressure estimation unit which estimates a blood pressure on the basis of a pressure in a specific time period and differences between a plurality of pulse wave signals measured in the specific time period due to the pressure.

16 Claims, 21 Drawing Sheets

(51) Int. Cl.
 *A61B 5/00* (2006.01)
 *A61B 5/021* (2006.01)
 *A61B 5/024* (2006.01)

(52) U.S. Cl.
 CPC ............ *A61B 5/742* (2013.01); *A61B 5/7475* (2013.01); *A61B 5/02116* (2013.01); *A61B 5/02416* (2013.01)

(56) References Cited

FOREIGN PATENT DOCUMENTS

| | | |
|---|---|---|
| JP | 62-38137 A | 2/1987 |
| JP | 5-158096 A | 6/1993 |
| JP | 2001-44552 A | 2/2001 |
| JP | 2004-121806 A | 4/2004 |
| JP | 2005-261505 A | 9/2005 |
| JP | 2005-288002 A | 10/2005 |
| JP | 2008-188303 A | 8/2008 |
| JP | 2012-71058 A | 4/2012 |
| JP | 2012-205673 A | 10/2012 |

OTHER PUBLICATIONS

Communication dated Apr. 1, 2017 issued by the State Intellectual Property Office of People's Republic of China in counterpart application No. 201580010819.9.

\* cited by examiner

BLOOD PRESSURE ESTIMATION DEVICE, BLOOD PRESSURE ESTIMATION METHOD, BLOOD PRESSURE MEASUREMENT DEVICE, AND RECORDING MEDIUM

CROSS REFERENCE TO RELATED APPLICATIONS

This application is a National Stage of International Application No. PCT/JP2015/000667 filed Feb. 13, 2015, claiming priority based on Japanese Patent Application No. 2014-025371 filed Feb. 13, 2014, the contents of all of which are incorporated herein by reference in their entirety.

TECHNICAL FIELD

The present invention relates to a blood pressure estimation device and the like that estimate blood pressure.

BACKGROUND ART

The oscillometric method, the Korotkoff method, and the like, for example, are known as blood pressure measurement methods. The amplitude of a pulse wave measured at an upper arm changes according to the pressure being applied to the upper arm while the internal pressure of a cuff is being changed. In the oscillometric method, a blood pressure in the course of heart contraction (systolic blood pressure) and a blood pressure in the course of heart expansion (diastolic blood pressure) are measured on the basis of the amplitude. Systolic blood pressure is also referred to as maximum blood pressure and hereinafter referred to as SBP. SBP stands for systolic-blood-pressure. Meanwhile, diastolic blood pressure is also referred to as minimum blood pressure and hereinafter referred to as DBP. DBP stands for diastolic-blood-pressure.

In the Korotkoff method, in accordance with a pressure is applied to an upper arm while the internal pressure of a cuff is being changed, Korotkoff sounds are generated in the pressurized artery, and the blood pressure is measured on the basis of the generation of the Korotkoff sounds. In particular, a kind of Korotkoff method in which a detector, such as a microphone, detects Korotkoff sounds are also called microphone method.

In a situation that includes, for example, body movement of a subject to be measured, external vibrations, or noise from a surrounding area, a blood pressure measurement device based on the oscillometric method or the Korotkoff method detects the noise or the like in addition to blood pressure. As a result, a signal measured by the blood pressure measurement device contains large noise. Accordingly, it is difficult to properly measure a systolic blood pressure and a diastolic blood pressure on the basis of such a signal measured by the blood pressure measurement device. In other words, to properly measure blood pressure by the use of the blood pressure measurement device, it is necessary to induce the subject to be measured to be in a rest state or to create a quiet environment.

The sphygmomanometer (blood pressure measurement device) disclosed in PTL 1 includes a blood pressure measurement means for measuring blood pressure of a subject to be measured, and a rest state inducing means for inducing the subject to be in a rest state on the basis of the breathing state of the subject to be measured. The rest state inducing means applies microwaves to the subject to be measured. The microwaves reflected from the subject to be measured undergo the Doppler shift due to a respiratory motion of the subject to be measured. The rest state inducing means calculates an actual expiration time and an actual inspiration time of the subject to be measured on the basis of the applied microwaves and the reflected microwaves, and induces the subject to be measured to a rest state on the basis of the ratio, total time or duration time of the expiration and inspiration times of the subject.

As described above, the blood pressure measurement device measures a pulse wave (pulse) containing noise in response to the subject to be measured coming in contact with a measurement region (specific region) used by the sphygmomanometer or the body movement of the subject to be measured.

PTL 2 discloses a non-invasive blood pressure measurement device capable of removing the noise and also relieving burden on a subject to be measured. The blood pressure measurement device has the function of removing noise from a measured pulse wave.

The blood pressure measurement device includes a cuff that measures, as a pulse wave, heartbeats at a body surface of the subject to be measured, multiple independent air bladders that set a uniform pressure condition for the cuff, and multiple pressure sensors each of which detects a pulse wave from a corresponding one of the air bladders. Each air bladder is connected to the corresponding one of the pressure sensors. The blood pressure measurement device also includes an arithmetic processing means for removing noise from the pulse waves measured by the pressure sensors by applying calculation according to a separation matrix method, adaptive filtering method, or both methods to the pulse waves.

The automatic blood pressure measurement device disclosed in PTL 3 properly measures a maximum blood pressure on the basis of a calculated amplitude ratio calculated using three expansion bags. The electronic sphygmomanometer disclosed in PTL 4 extracts a pulse wave while the internal pressure of a cuff is being reduced, and calculates the amplitude of the extracted pulse wave. The electronic sphygmomanometer determines whether the internal pressure of the cuff is insufficient, on the basis of whether the calculated amplitude is equal to or smaller than a threshold value. The blood pressure measurement device disclosed in PTL 5 measures pulse waves with multiple pulse wave sensors and calculates the time point at which the pulse wave having the largest amplitude among the measured pulse waves started. The blood pressure measurement device calculates the internal pressure of the cuff at the time point thus calculated, as a maximum blood pressure.

CITATION LIST

Patent Literature

PTL 1: Japanese Patent Application Laid-open Publication No. 2012-205673
PTL 2: Japanese Patent Application Laid-open Publication No. 2005-288002
PTL 3: Japanese Patent Application Laid-open Publication No. 2012-71058
PTL 4: Japanese Patent Application Laid-open Publication No. 2008-188303
PTL 5: Japanese Patent Application Laid-open Publication No. S62(1987)-038137

SUMMARY OF INVENTION

Technical Problem

First, although the sphygmomanometer disclosed in PTL 1 induces the subject to be measured to be in a rest state, the sphygmomanometer detects noise, for example, when the subject to be measured is walking, when the subject to be measured is psychologically stressed, or when the measurement environment is noisy and causes vibration noise. Hence, it is difficult for the sphygmomanometer to properly measure blood pressure.

Further, the blood pressure measurement device disclosed in PTL 2 includes multiple air bladders and multiple pressure sensors. Hence, the blood pressure measurement device has a complex structure. In addition to this, it is difficult to appropriately arrange the air bladders and the sensors for measuring pulse waves in the blood pressure measurement device. Even when the arithmetic processing means removes noise from pulse waves, the blood pressure measurement device may be affected by noise that the arithmetic processing means failed to remove, for example, noise having the same frequency components as those of the pulse waves, in particular. Hence, the blood pressure measurement device may not be able to properly measure blood pressure.

In addition, the blood pressure measurement device disclosed in PTL 3 has a complex structure of including three expansion bags in the cuff. Further, the blood pressure measurement device fails to properly measure blood pressure when the pressure being applied to the cuff changes even a little due to the movement of the subject to be measured or the like. The electronic sphygmomanometer disclosed in PTL 4 determines whether the internal pressure of the cuff is insufficient, on the basis of a single extracted pulse wave, and hence, the sphygmomanometer may not operate appropriately when the pulse wave is affected by noise. Further, the blood pressure measurement device disclosed in PTL 5 calculates blood pressure on the basis of the pulse wave having the largest amplitude, and may hence fail to properly measure blood pressure when the pulse wave is affected by noise.

Accordingly, the present invention mainly aims to provide a blood pressure estimation device and the like for estimating blood pressure with a high degree of accuracy.

Solution to Problem

As an aspect of the present invention, a blood pressure estimation device including:

blood pressure estimation means for estimating a blood pressure on the basis of a pressure in a certain time period and difference between a plurality of pulse wave signals measured in association with the pressure.

In addition, as another aspect of the present invention, a blood pressure estimation method including; estimating, by using an information processing device, a blood pressure on the basis of a pressure in a certain time period and difference between a plurality of pulse wave signals measured in association with the pressure in the certain time period.

Furthermore, the object is also realized by a blood pressure estimation program, and a computer-readable recording medium which records the program.

Advantageous Effects of Invention

According to the blood pressure estimation device and the like of the present invention, it is possible to estimate blood pressure with a high degree of accuracy.

Next, exemplary embodiments of the present invention will be described in detail with reference to the drawings.

<First Exemplary Embodiment>

Figure 1:
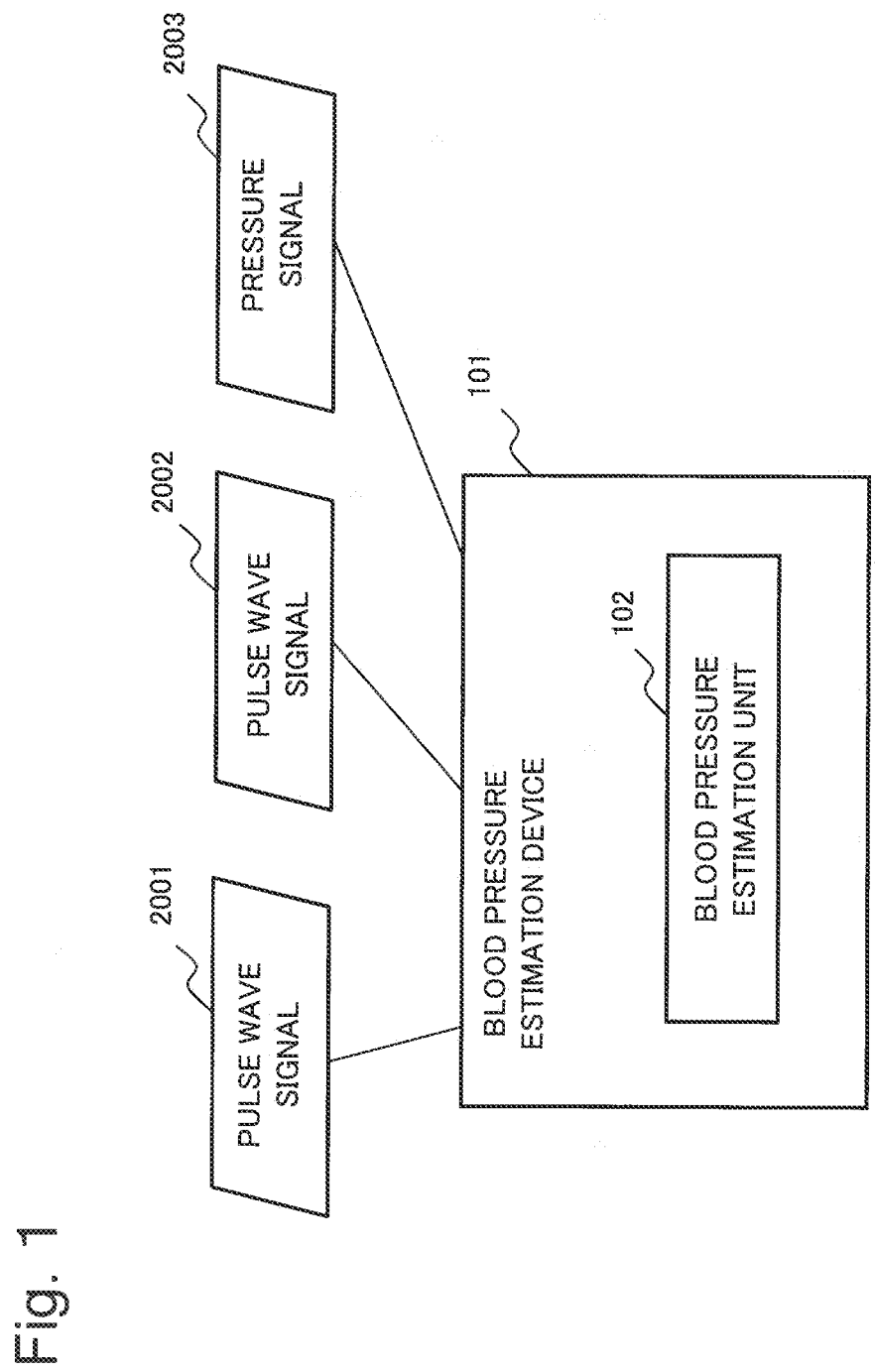
FIG. 1 is a block diagram illustrating a configuration of a blood pressure estimation device according to a first exemplary embodiment of the present invention.
Figure 2:
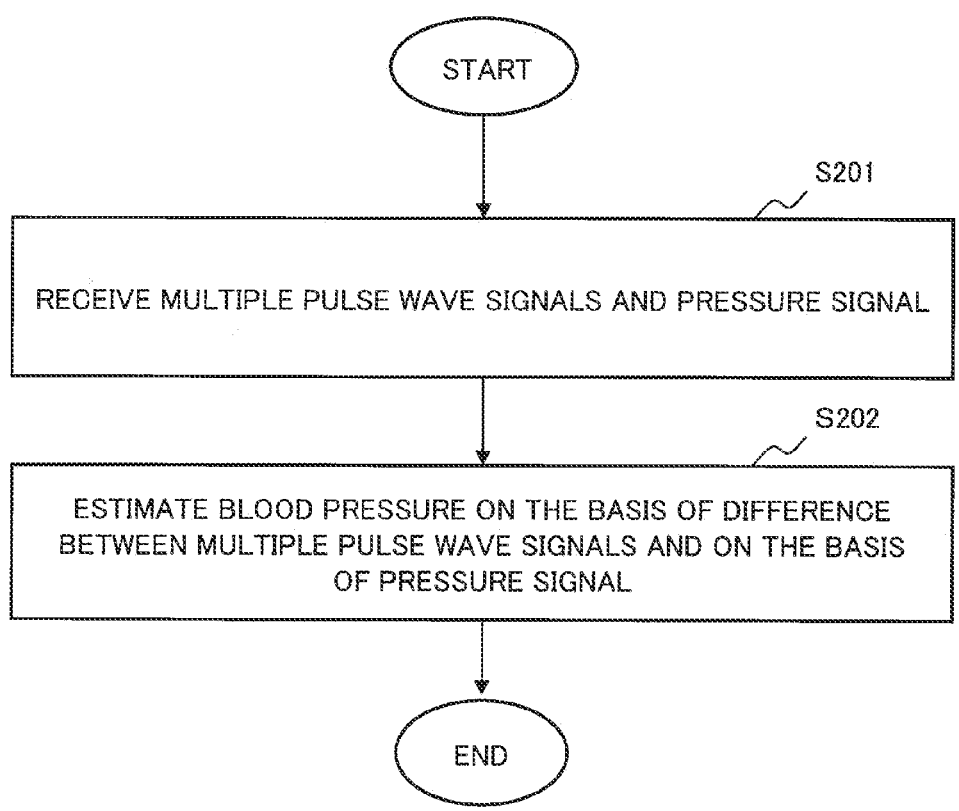
FIG. 2 is a flowchart presenting a flow of a process by the blood pressure estimation device according to the first exemplary embodiment.

Detailed description will be given of a configuration of a blood pressure estimation device 101 according to a first exemplary embodiment of the present invention and a processing executed by the blood pressure estimation device 101, with reference to FIG. 1 and FIG. 2. FIG. 1 is a block diagram illustrating the configuration of the blood pressure estimation device 101 according to the first exemplary embodiment of the present invention. FIG. 2 is a flowchart presenting a flow of the process by the blood pressure estimation device 101 according to the first exemplary embodiment.

The blood pressure estimation device 101 according to the first exemplary embodiment includes a blood pressure estimation unit 102.

The blood pressure estimation device 101 receives a pressure signal 2003 indicating the pressure in a certain time period and multiple pulse wave signals measured while the pressure is being applied to a subject to be measured in the certain time period (Step S201).

In the following, for convenience of description, the multiple pulse wave signals are assumed to be two pulse wave signals (i.e., a pulse wave signal 2001 and a pulse wave signal B). The number of pulse wave signals that the blood pressure estimation device 101 according to this exemplary embodiment receives may be three or more as described later.

Next, the blood pressure estimation unit 102 estimates a blood pressure (blood pressure value) on the basis of the pressure signal 2003 and the difference between the pulse wave signal 2001 and the pulse wave signal B (Step S202).

Here, the blood pressure is systolic blood pressure, diastolic blood pressure, or both. Systolic blood pressure is a blood pressure obtained when the heart contracts and thereby pumps blood out to the arteries. In contrast, diastolic blood pressure is a blood pressure measured when the heart expands and thereby lets blood flow gently to the arteries.

Figure 5:
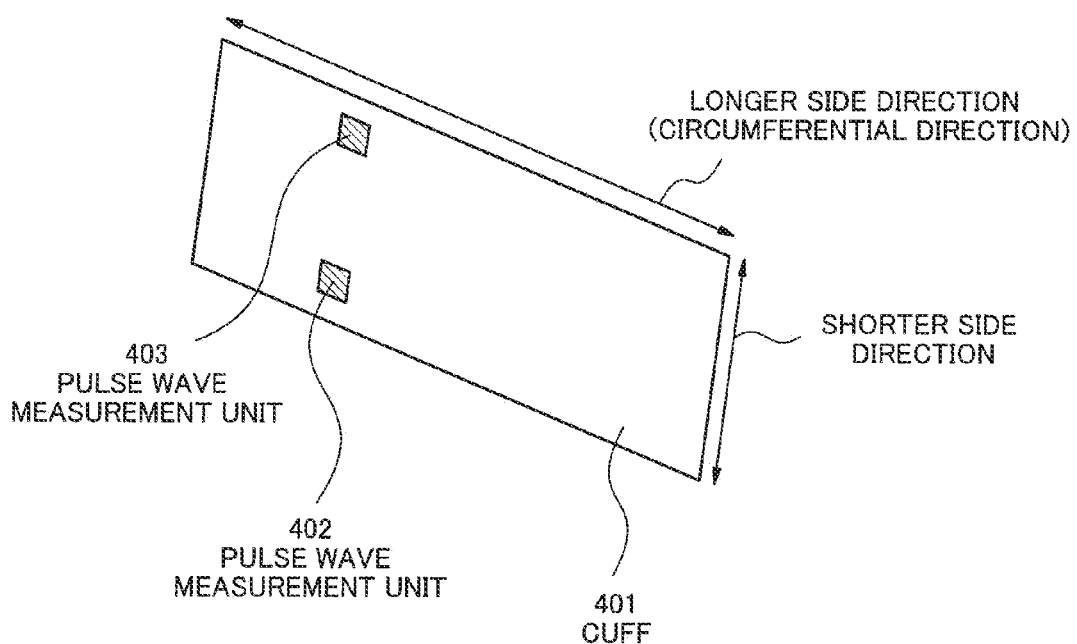
FIG. 5 is a perspective view around a cuff that is not attached to anything.

In the following, for convenience of description, it is assumed that the shape of a cuff is a rectangle (rectangular shape), a trapezoid, or a shape close to a rectangular shape in an exploded state, as illustrated in FIG. 5 to be described later. A shape close to a rectangular shape is one in which the cuff is tapered or being in an arc in either of or both of the shorter side direction and the longer side direction, for example. However, a shape close to a rectangular shape is not limited to the above-described shapes. The longer side direction is assumed to be the direction of the cuff in which the cuff is wrapped around a specific region, i.e., the circumferential direction of the cuff in a state where the cuff is wrapped around the specific region. The shorter side direction is assumed to be a direction orthogonal (or substantially orthogonal) to the longer side direction. Moreover, the entire cuff or part of the cuff is assumed to apply pressure to the specific region in a pressurized state. In this case, "upstream" is assumed to indicate the part of arteries between the center or the heart and the shorter-side direction center of the cuff. "Downstream" is assumed to indicate the part of arteries between the shorter-side direction center of the cuff and a peripheral side (e.g., a hand or a foot). However, examples of the cuff are not limited to those described above.

Figure 3:
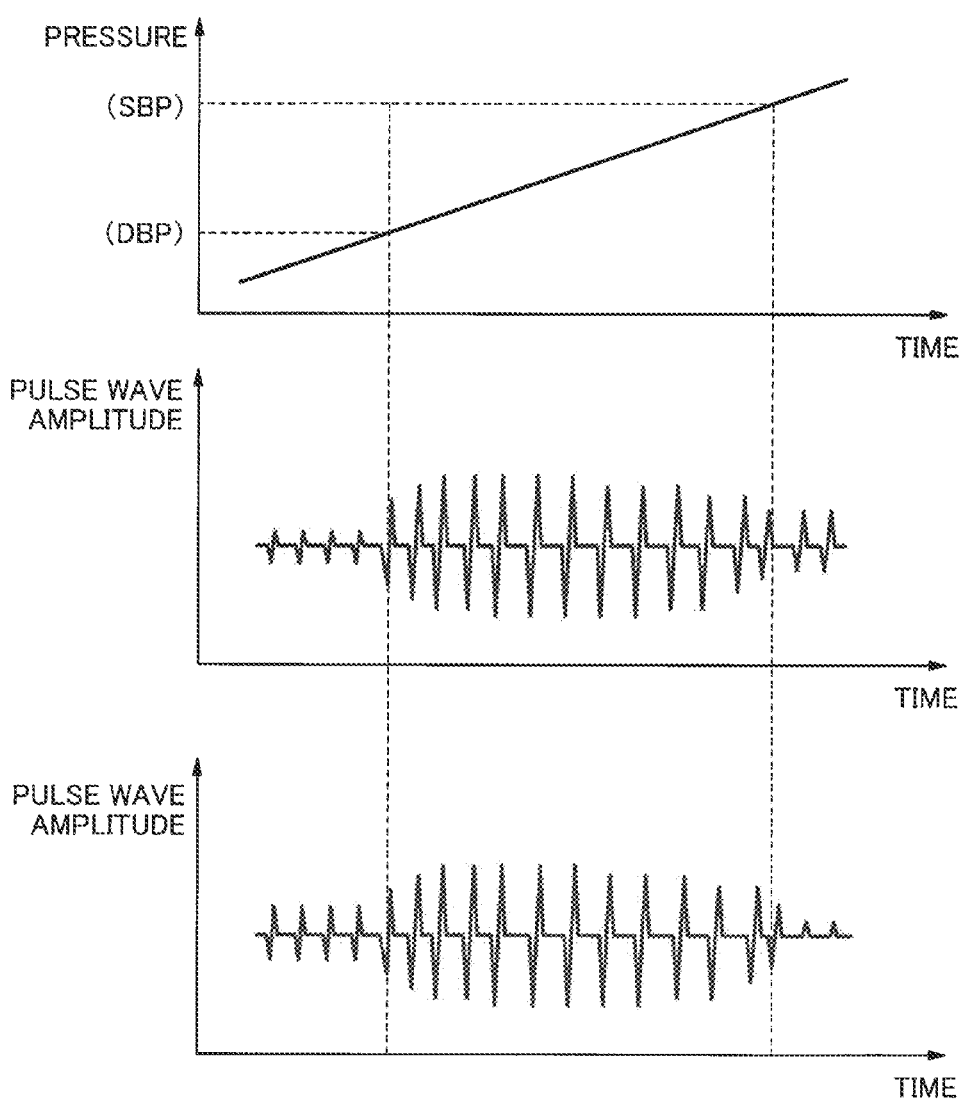
FIG. 3 is a figure schematically illustrating examples of pulse wave signals.

For example, the blood pressure estimation unit 102 receives the two pulse wave signals (referred to as "pulse wave signal AA" and "pulse wave signal BB" for convenience of description) illustrated in FIG. 3. FIG. 3 presents graphs schematically illustrating examples of the pulse wave signals that the blood pressure estimation unit 102 receives. Each horizontal axis in FIG. 3 represents time and indicates a later time at a rightward position. The vertical axis in the upper graph in FIG. 3 represents the amplitude of the pressure signal and indicates a larger amplitude at a higher position. The vertical axis in each of the middle and lower graphs in FIG. 3 represents the amplitude of the corresponding pulse wave signal, and indicates a larger amplitude at a position closer to the upper end or the lower end of the graph while indicating a smaller amplitude at a position closer to the center between the upper edge and the lower edge. In the case of the example in FIG. 3, the certain time period is, for example, a time period in which the heart pulses (heart beats) multiple times.

For example, the blood pressure estimation unit 102 estimates the pressure when the difference between the pulse wave signal AA and the pulse wave signal BB is the largest or when the absolute value of the difference is the largest (or around the largest), as a systolic blood pressure.

For example, a definition of "around the largest" may be a value within a certain range from the largest. The certain range may include values determined in advance, or values calculated under the condition, for example, that the inclination of the target for calculating the largest value (e.g., the above-described difference) (obtained by differentiation or calculating finite difference) is smaller than a predetermined value. The certain range is not limited to the above-described examples.

The heart pumps a large amount of blood out to the arteries in a systolic period. In this case, since much blood flows into the arteries at once, the pressure in the arteries changes according to the amount of the blood pumped out. Specifically, the amount of blood pumped out is large at the upstream while being small at the downstream. As a result of this, a pulse wave signal measured at the upstream and a pulse wave signal measured at the downstream are different from each other. Hence, the blood pressure estimation unit 102 can estimate the pressure obtained when the difference between the pulse wave signal AA and the pulse wave signal BB is the largest (or around the largest), as a systolic blood pressure.

The blood pressure estimation unit 102 estimates the pressure that is lower than the systolic blood pressure and obtained when the difference between the pulse wave signal AA and the pulse wave signal BB is smaller than a certain value, as a diastolic blood pressure.

The certain value is, for example, a value that is several percent or some tens of percent of the largest value larger than the average value of the differences each between the pulse wave signal AA and the pulse wave signal BB in the case where no pressure is applied. Alternatively, the certain value may be a value that is several milliseconds (ms) to some tens of milliseconds larger than the average value of the differences each between the pulse wave signal AA and the pulse wave signal BB in the case where no pressure is applied. Alternatively, the certain value may be a value calculated on the basis of a diastolic blood pressure measured in accordance with a procedure of the oscillometric method, the Korotkoff method, or the like. The certain value is not limited to the above-described examples.

The procedure for estimating a diastolic blood pressure is not limited to the above-described example. For example, the pressure obtained when an approximate curve computed on the basis of the relationship between time and the difference between the pulse wave signal AA and the pulse wave signal BB takes a certain value, is estimated as a diastolic blood pressure. The approximate curve may be multiple linear approximate straight lines having different inclinations and sections for respective pressure ranges, or a polynomial approximate curve applicable to a pressure range equal to or smaller than the systolic blood pressure. However, the approximate curve is not limited to these. The certain value may be, for example, 0 ms, but is not limited to this.

The heart lets blood flow gently into the arteries in a diastolic period. In this case, since the blood flows gently into the arteries, the pressure in the arteries does not change to a large extent. Consequently, the difference between a pulse wave signal measured at the upstream and a pulse wave signal measured at the downstream is small. Accordingly, the blood pressure estimation unit 102 can estimate, as a diastolic blood pressure, a pressure that is lower than the systolic blood pressure and is obtained when the difference between the pulse wave signal AA and the pulse wave signal BB is smaller than the certain value.

The blood pressure estimation unit 102 may calculate the difference to detect by the use of a value such as a ratio instead of the difference. In this case, the blood pressure estimation unit 102 estimates blood pressure on the basis of the value of the ratio. The difference to detect may be any index by the use of which the pulse wave signal AA and the pulse wave signal BB can be compared, and is hence not limited the above-described example.

The blood pressure estimation device 101 estimates a blood pressure on the basis of the difference between the pulse wave signal AA and the pulse wave signal BB. With this configuration, even when, for example, the pulse wave signal AA and the pulse wave signal BB contain similar noises, the blood pressure estimation device 101 estimates the blood pressure on the basis of the difference to thereby reduce the noises. Hence, the blood pressure estimation device 101 can estimate blood pressure with a high degree of accuracy by reducing the influence of noise.

Conversely, common blood pressure estimation devices are not capable of accurately measuring blood pressure when measured pulse waves contain noise as described above.

In other words, with the blood pressure estimation device 101 according to this exemplary embodiment, it is possible to estimate blood pressure with a high degree of accuracy.

Figure 4:
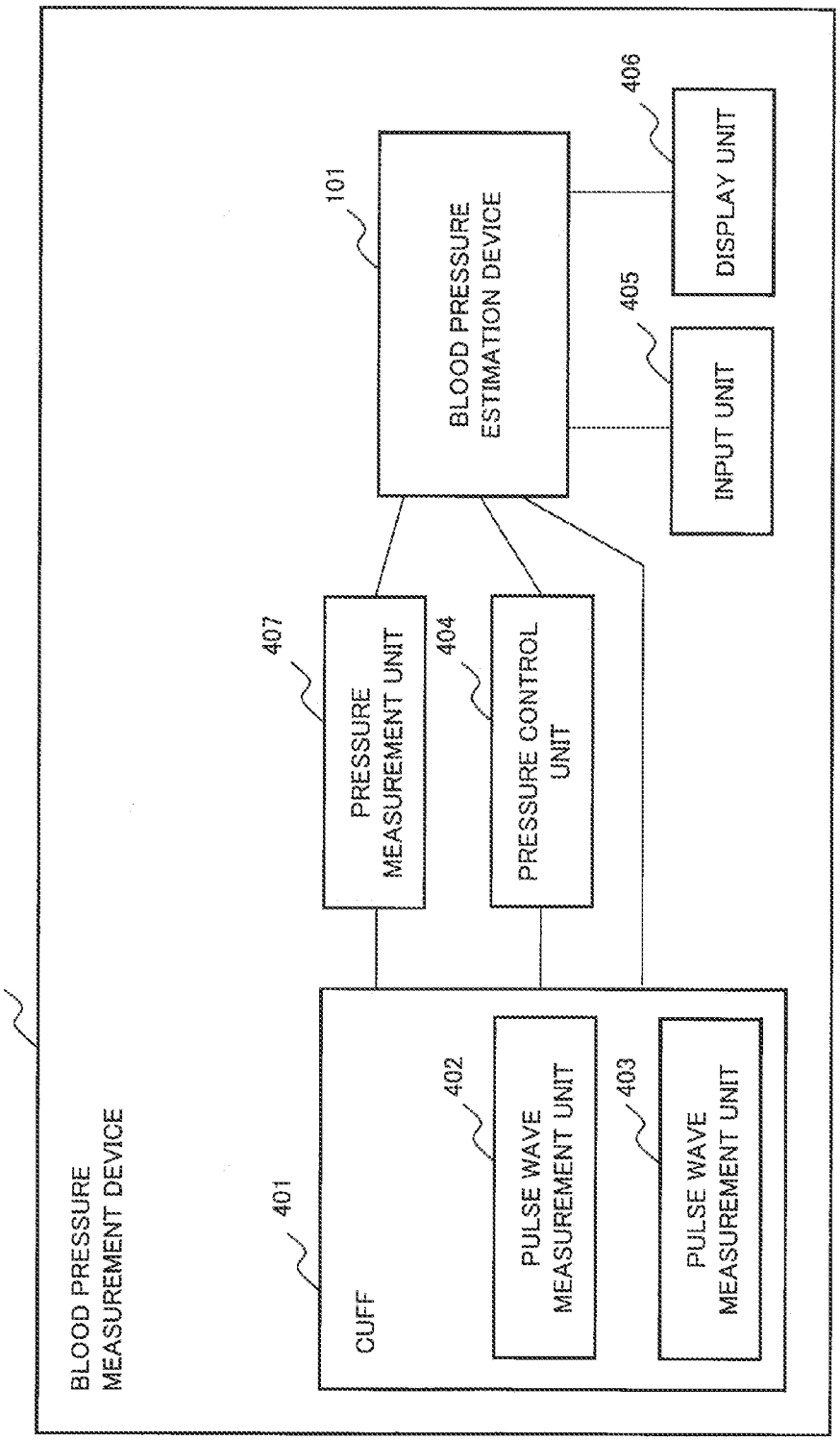
FIG. 4 is a block diagram illustrating a configuration of the blood pressure measurement device according to the first exemplary embodiment.

For example, the blood pressure estimation device 101 receives the pressure signal 2003 measured by a blood pressure measurement device 408 illustrated in FIG. 4 and multiple pulse wave signals measured by the blood pressure measurement device 408. FIG. 4 is a block diagram illustrating a configuration of the blood pressure measurement device 408 according to the first exemplary embodiment.

The blood pressure measurement device 408 includes a cuff 401, a pulse wave measurement unit 402, a pulse wave measurement unit 403, a pressure measurement unit 407, a pressure control unit 404, an input unit 405, a display unit 406, and the blood pressure estimation device 101. As illustrated in FIG. 5, the cuff 401, the pulse wave measurement unit 402, and the pulse wave measurement unit 403 are integrally formed. FIG. 5 is a perspective view around the cuff 401 that is not attached to anything.

Figure 6:
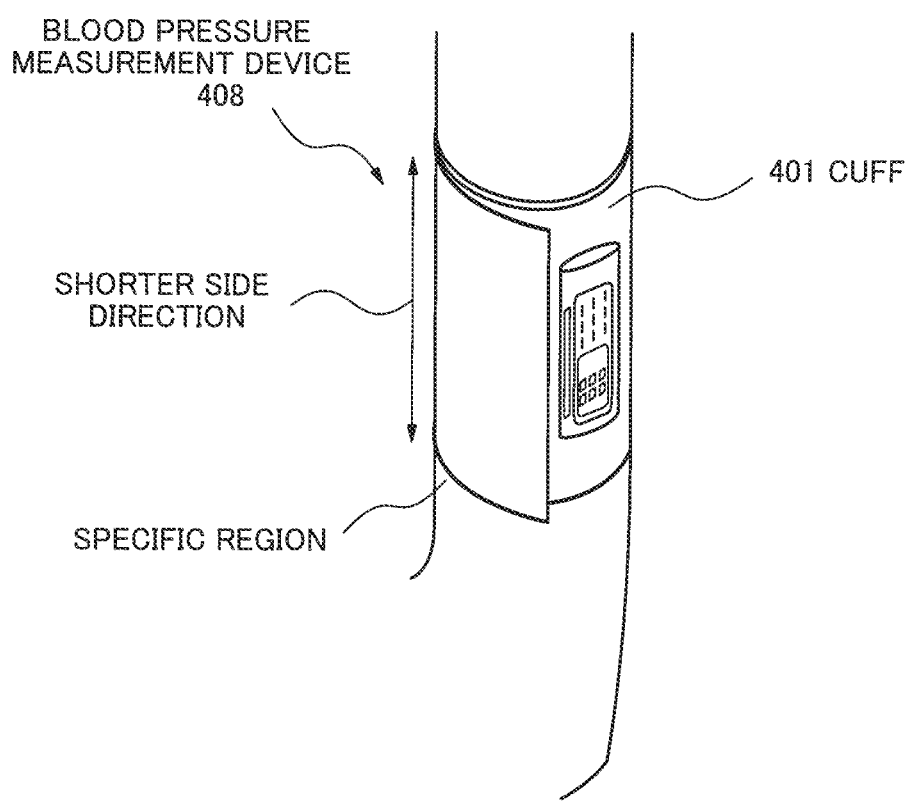
FIG. 6 is a diagram illustrating an example of a state of a cuff being attached to a specific region.

As illustrated in FIG. 6, a subject to be measured first wraps the cuff 401 around a specific region, such as the upper arm, a part of the leg, or the wrist, to measure blood pressure. The subject to be measured attaches the cuff 401 by wrapping the cuff 401 in the longer side direction around the specific region. FIG. 6 is a diagram illustrating an example of a state of the cuff 401 being attached to a specific region.

In this case, it is assumed that the artery is parallel (or substantially parallel) with the shorter side direction of the cuff 401. In other words, the pulse wave measurement unit 402 and the pulse wave measurement unit 403 are at respective positions at the upstream and downstream of the artery.

The pulse wave measurement unit 402 and the pulse wave measurement unit 403 are, for example, vibration sensors that detect vibrations caused by pulsation or photoelectric sensors that detect reflected light when light (such as visible light or far-red light) is applied to the specific region or that detect transmitted light when light is applied to the specific region. The pulse wave measurement unit 402 and the pulse wave measurement unit 403 may be sensors different from each other. For example, the pulse wave measurement unit 402 may be a photoelectric sensor for a first wavelength, and the pulse wave measurement unit 403 may be a photoelectric sensor for a second wavelength different from the first wavelength. The pulse wave measurement unit 402 and the pulse wave measurement unit 403 are not limited to the above-described examples. For example, magnetic sensors or acceleration sensors may be used as the pulse wave measurement unit 402 and the pulse wave measurement unit 403. The pulse wave measurement unit 402 and the pulse wave measurement unit 403 may be pressure sensors. When pressure sensors are used, pressure is divided into signals having different cycles, through Fourier transform, for example. When the pressure control unit 404 applies pressure or reduces pressure at a uniform (or substantially uniform) speed, the cycle of the pressure associated with the pressure control unit 404 is long. Accordingly, each of the pulse wave measurement unit 402 and the pulse wave measurement unit 403 extracts a signal having a short cycle from the pressure, in combination with a filter circuit or the like or by the use of a digital filter, to extract a pulse wave signal deriving from a pulse wave.

The subject to be measured operates the input unit 405 to start measurement. The input unit 405 includes a measurement start button for starting measurement, a power button, and a measurement stop button for stopping measurement after measurement start, as well as a left button, a right button, and the like to be used for selecting an item displayed on the display unit 406 (none of the buttons are depicted). The input unit 405 transmits an input signal received from the subject to be measured or the like to the blood pressure estimation device 101.

In response to the start of blood pressure measurement, the pressure control unit 404, for example, controls the amount of gas (e.g., air) or liquid, or the amounts of both to be filled in the cuff 401, by referring to the internal pressure of the cuff 401 measured by the pressure measurement unit 407, to thereby control the pressure being applied to the specific region. For example, the pressure control unit 404 controls the operation of a pump that transfers gas to be filled into the cuff 401 or the operation of a valve in the cuff 401.

The cuff 401 may include a pressure bag 1006, such as a pressure bag (air bag) into which gas is filled or a gel bag into which gel or liquid is filled. The cuff 401 applies pressure to the specific region in accordance with the control by the pressure control unit 404.

Figure 7A:
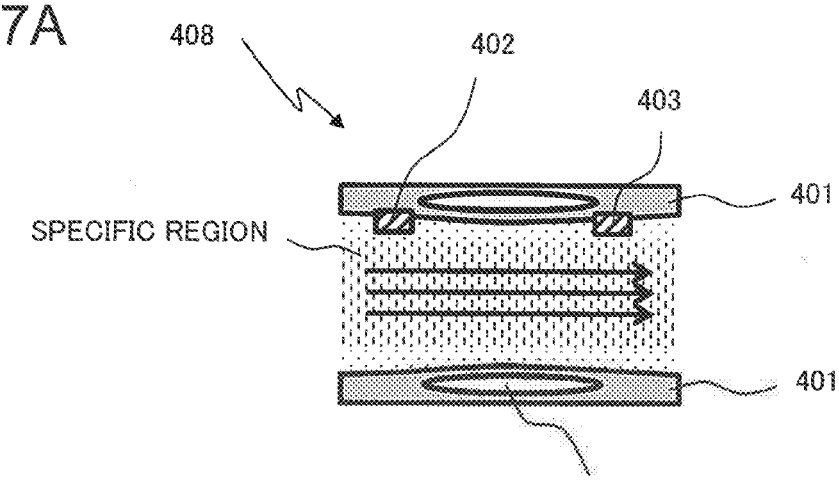
FIG. 7A is a diagram schematically illustrating an example of a positional relationship between a cuff and pulse wave measurement units.

The pulse wave measurement unit 402 and the pulse wave measurement unit 403 may be arranged so that the shorter-side direction center (or substantially center) of pressure application in the cuff 401 is located between the pulse wave measurement unit 402 and the pulse wave measurement unit 403. FIG. 7A is a diagram schematically illustrating an example of a positional relationship between the cuff and the pulse wave measurement unit. An optimal arrangement of the pulse wave sensors is the case where the pulse wave measurement unit 402 and the pulse wave measurement unit 403 are positioned at respective fringes of the pressure bag 1006. Specifically, in this arrangement, the pulse wave measurement unit 402 and the pulse wave measurement unit 403 are positioned in a pressure unit where pulse wave signals can easily be measured, and the pulse wave signals have a large difference. For convenience of description, FIG. 7A includes a specific region and a blood flow and the like in the specific region. However, the blood pressure measurement device 408 does not include any specific region and any blood flow and the like in a specific region.

Figure 7B:
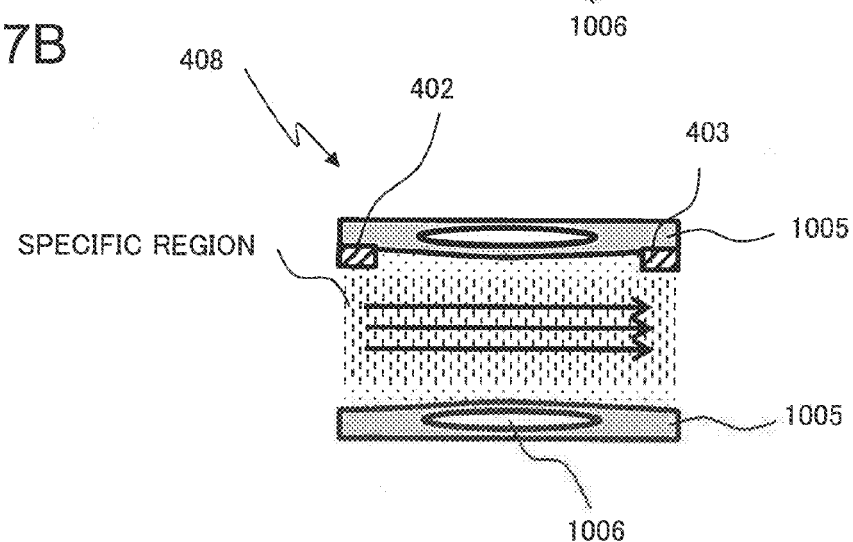
FIG. 7B is a diagram schematically illustrating an example of a positional relationship between a cuff and pulse wave measurement units.

FIG. 7B is a diagram schematically illustrating an example, which is different from that in FIG. 7A, of the positional relationship between the cuff and the pulse wave measurement units. FIG. 7B illustrates an arrangement in which the pulse wave measurement unit 402 and the pulse wave measurement unit 403 are located at positions at respective fringes of the cuff so that the difference between pulse wave signals measured by the pulse wave measurement unit 402 and the pulse wave measurement unit 403 is to be the largest. For convenience of description, FIG. 7B includes a specific region and a blood flow and the like in the specific region. However, the blood pressure measurement device 408 does not include any specific region and any blood flow and the like in a specific region.

Figure 7C:
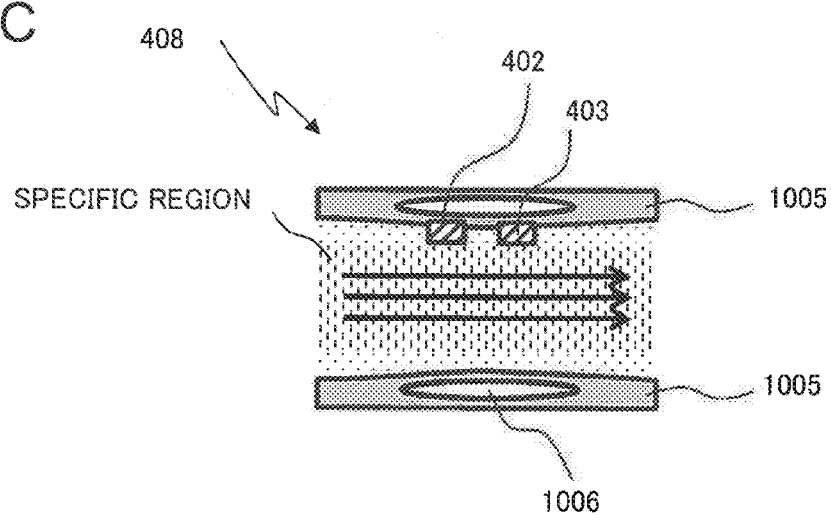
FIG. 7C is a diagram schematically illustrating an example of a positional relationship between a cuff and pulse wave measurement units.

FIG. 7C is a diagram schematically illustrating an example of the positional relationship between the cuff and the pulse wave measurement units. FIG. 7C illustrates an arrangement in which the pulse wave measurement unit 402 and the pulse wave measurement unit 403 are provided around the center (or substantially center) of the pressing unit. In the arrangement, the pulse wave measurement unit 402 and the pulse wave measurement unit 403 can easily measure pulse wave signals. For convenience of description, FIG. 7C includes a specific region and a blood flow and the like in the specific region. However, the blood pressure measurement device 408 does not include any specific region and any blood flow and the like in a specific region.

The positional relationship between the cuff and the pulse wave measurement units is not limited to any of the above-described examples and may be one configured so as to be able to measure pulse wave signals and the difference easily. It is easier for each pulse wave measurement unit to measure a pulse wave when the pulse wave measurement unit is located closer to the center (or substantially center) of the pressing unit and to measure the difference when the pulse wave measurement unit is located further away from the center (or substantially center) of the pressing unit (i.e., close to the corresponding fringe of the cuff). For example, the arrangement may be one in which the pulse wave measurement unit 402 is provided at an fringe of the pressing unit while the pulse wave measurement unit 403 is provided at a side of the cuff, or one in which the pulse wave measurement unit 402 is provided at an fringe of the pressing unit while the pulse wave measurement unit 403 is provided around the center of the pressing unit. Alternatively, the arrangement may be one in which the pulse wave measurement unit 402 is provided at a fringe of the cuff while the pulse wave measurement unit 403 is provided at an fringe of the pressing unit, or one in which the pulse wave measurement unit 402 is provided at a fringe of the cuff and the pulse wave measurement unit 403 is provided around the center of the pressing unit. Further, the arrangement may be one in which the pulse wave measurement unit 402 is provided around the center of the pressing unit while the pulse wave measurement unit 403 is provided at an fringe of the pressing unit, or one in which the pulse wave measurement unit 402 is provided around the center of the pressing unit while the pulse wave measurement unit 403 is provided at a fringe of the cuff.

Next, each of the pulse wave measurement unit 402 and the pulse wave measurement unit 403 measures a pulse wave at the specific region while the pressure control unit 404 controls the pressure being applied to the specific region.

The pulse wave measurement unit 402 and the pulse wave measurement unit 403 transmits the measured pulse waves as pulse wave signals (i.e., a pulse wave signal A and a pulse wave signal B) to the blood pressure estimation device 101. The pressure measurement unit 407 transmits a measured pressure as the pressure signal 2003 to the blood pressure estimation device 101.

For example, the pressure measurement unit 407 converts the measured pressure to a digital signal through digitization (analog-digital conversion, A/D conversion) and then transmits the digital signal as the pressure signal 2003. Similarly, each of the pulse wave measurement unit 402 and the pulse wave measurement unit 403 converts the measured pulse wave to a digital signal through digitization and then transmits the digital signal as a pulse wave signal.

Part of the pressure (or pulse wave) may be extracted by performing A/D conversion on the signal by the use of a filter or the like for extracting a certain frequency. Alternatively, the pressure (or pulse wave) may be amplified to have a certain amplitude by the use of an amplifier or the like.

Subsequently, the blood pressure estimation device 101 carries out the above-described process to estimate blood pressure. In this process, the blood pressure estimation device 101 may transmit a control signal representing the control to be performed to the pressure control unit 404.

The display unit 406 displays the blood pressure measured by the blood pressure estimation device 101. The display unit 406 is, for example, a liquid crystal display (LCD), an organic light-emitting diode (OLED), or an electronic paper. An electronic paper can be realized by, for example, those based on a microcapsule system, an electronic powder and granular material system, a cholesteric liquid crystal system, an electrophoretic system, an electrowetting system, or the like.

The blood pressure measurement device 408 has a similar configuration as that of the blood pressure estimation device 101 and can hence obtain the similar effects to those of the blood pressure estimation device 101. In other words, the blood pressure measurement device 408 according to the first exemplary embodiment can measure blood pressure with a high degree of accuracy.

The blood pressure measurement device 408 may have a configuration that the blood pressure estimation device 101, the pulse wave measurement unit 402, the pulse wave measurement unit 403, and the like transmit and receive pulse wave signals via a communication network. The blood pressure measurement device 408 may have a configuration that the input unit 405 and the display unit 406 are provided outside the blood pressure measurement device 408 and are connected to the blood pressure measurement device 408 via a communication network.

The specific region may be an upper arm, a wrist, or the like. For example, when the specific region is a wrist, the pulse wave measurement unit 402 and the pulse wave measurement unit 403 may detect pulse waves via the radial artery.

<Second Exemplary Embodiment>

Next, a second exemplary embodiment of the present invention based on the above-described first exemplary embodiment will be described.

In the following description, the characteristic parts of the present exemplary embodiment are mainly described, and the same components as in the above-described first exemplary embodiment are assigned with the same reference signs, whereby overlapping description will be omitted.

Figure 8:
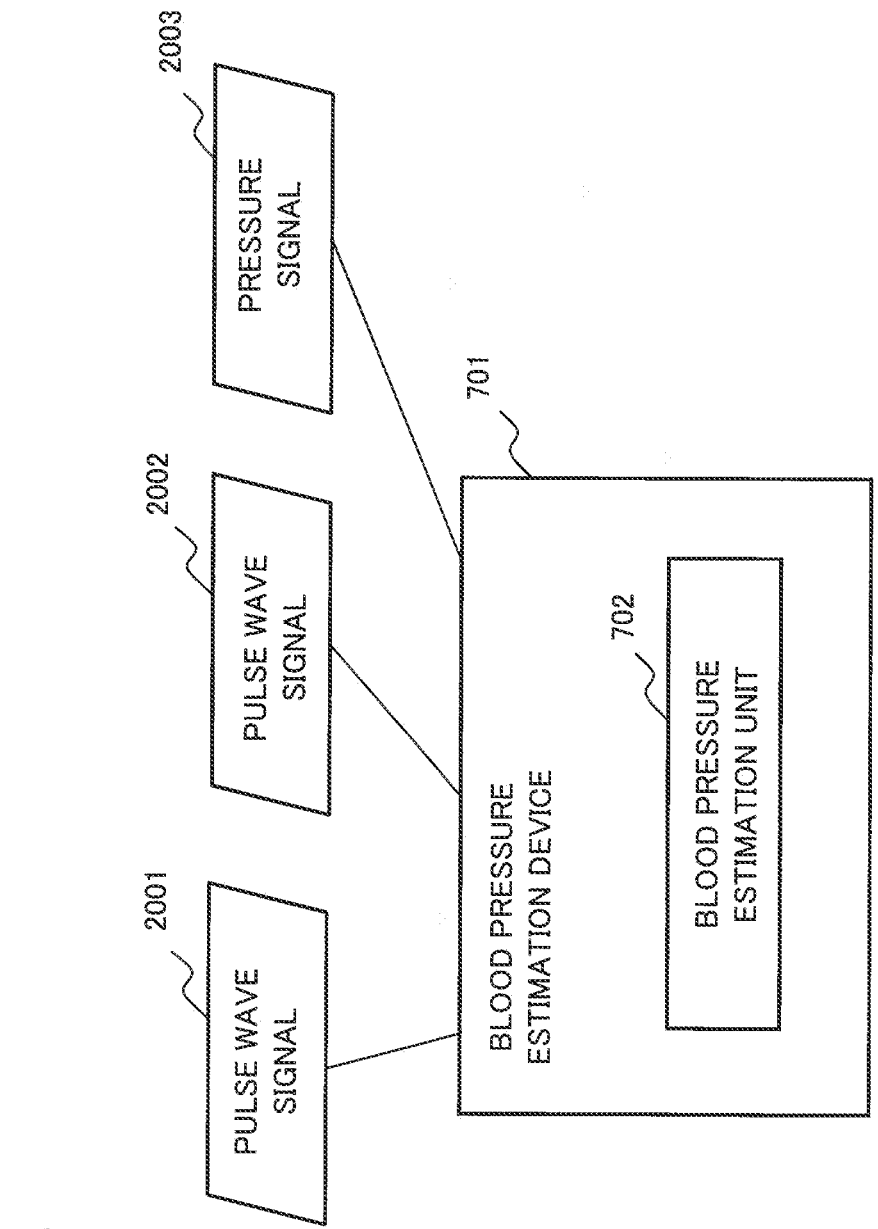
FIG. 8 is a block diagram illustrating a configuration of a blood pressure estimation device according to a second exemplary embodiment of the present invention.
Figure 9:
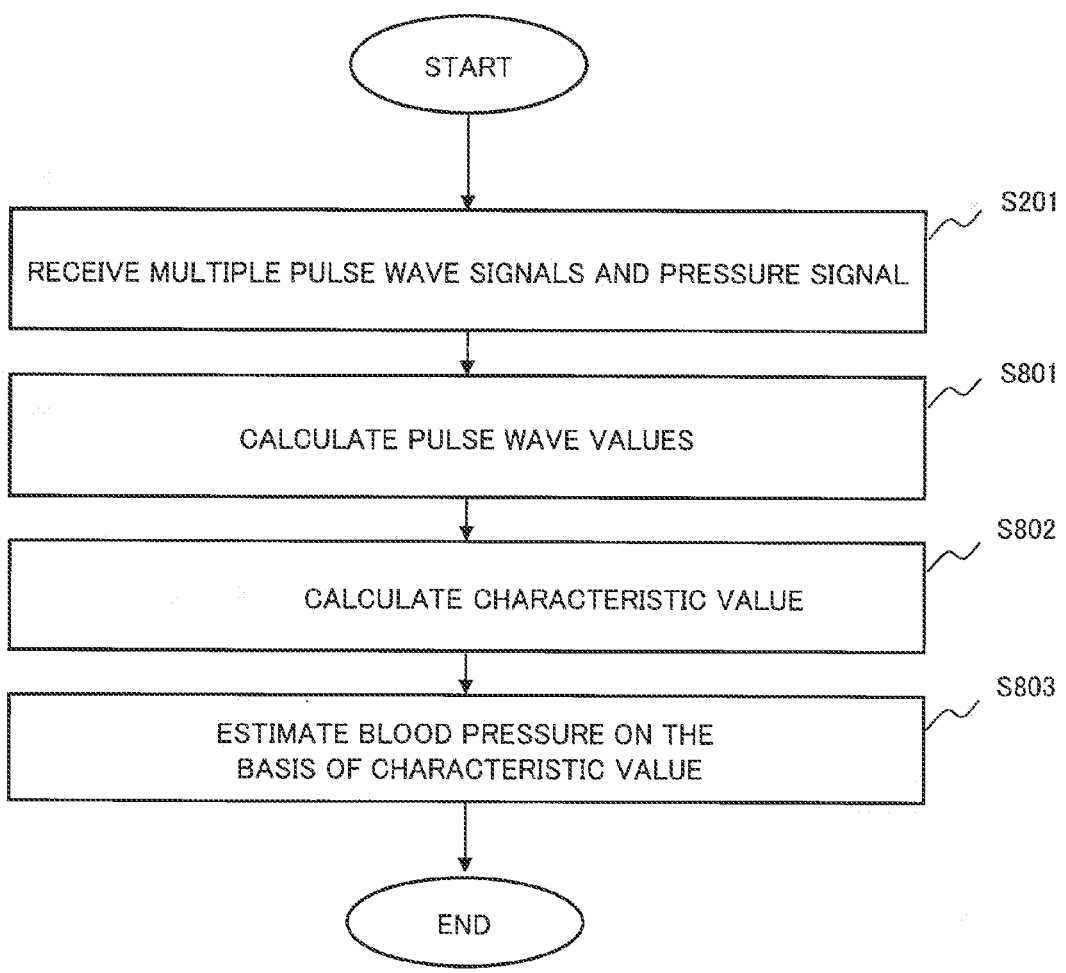
FIG. 9 is a flowchart presenting a flow of processes by a blood pressure estimation device according to the second exemplary embodiment.

With reference to FIG. 8 and FIG. 9, description will be given of a configuration of a blood pressure estimation device 701 according to the second exemplary embodiment and a processing executed by the blood pressure estimation device 701. FIG. 8 is a block diagram illustrating the configuration of the blood pressure estimation device 701 according to the second exemplary embodiment of the present invention. FIG. 9 is a flowchart presenting the flow of the process by the blood pressure estimation device 701 according to the second exemplary embodiment.

The blood pressure estimation device 701 according to the second exemplary embodiment includes a blood pressure estimation unit 702.

The blood pressure estimation unit 702 calculates pulse wave values each related to a pulse wave signal (a pulse wave signal 2001 or a pulse wave signal 2002) (Step S801).

Examples of the pulse wave value are Pulse wave value 1 to Pulse wave value 6 described below. Specifically, the examples are:
- extremum (i.e., the local maximum value, the local minimum value, or both) of the pulse wave signal, or the timing around the extremum (approximate extremum) . . . (Pulse wave value 1)
- amplitude value of the pulse wave signal . . . (Pulse wave value 2)
- timing at which the pulse wave signal rises (starts to increase) . . . (Pulse wave value 3)
- timing at which the pulse wave signal falls (starts to decrease) . . . (Pulse wave value 4)
- amplitude of the pulse wave signal on which frequency space (frequency domain) transform is performed, in the frequency space . . . (Pulse wave value 5)
- phase of the pulse wave signal on which frequency space transform is performed, in the frequency space . . . (Pulse wave value 6).

For example, a definition of "around the extremum" may be a value within a certain range from the extremum. The certain range may include values calculated on the basis of the condition, for example, that the degree of inclination with respect to that target for which an extremum is to be calculated (obtained by differentiation or calculating finite difference, for example) is smaller than a predetermined value. The certain range is not limited to the above-described example.

The blood pressure estimation unit 702 calculates Pulse wave value 1 to Pulse wave value 4 for a part corresponding to a single heartbeat in the pulse wave signal. For example, the blood pressure estimation unit 702 may calculate Pulse wave value 1 to Pulse wave value 4 by extracting a pulse wave signal having a certain cycle from the pulse wave signal. Pulse wave value 1 to Pulse wave value 4 have good characteristics that analysis of each pulse wave value is simple and does not take a long time.

Meanwhile, Pulse wave value 5 and Pulse wave value 6 are each a pulse wave value related to multiple frequency components in a part corresponding to a single heartbeat in the pulse wave signal. Pulse wave value 5 and Pulse wave value 6 have good characteristics that each pulse wave value can be calculated even when the pulse wave signal includes various frequencies.

Each pulse wave value may be defined when the pulse wave signal or a signal derived from the pulse wave signal, through, for example, differentiation or calculation of finite difference of the pulse wave signal, satisfies a predetermined condition, and is hence not limited to the above-described examples.

A method of transforming a pulse wave signal into a frequency space (frequency domain) is, for example, a short-time Fourier transform, or wavelet transform. Short-time Fourier transform, wavelet transform, and the like are common techniques, and hence description thereof is omitted in this exemplary embodiment.

The blood pressure estimation unit 702 then calculates the difference in pulse wave value calculated in Step S801 between the pulse wave signal 2001 and the pulse wave signal 2002, as a characteristic value (Step S802).

The blood pressure estimation unit 702 calculates, as the difference, the difference between corresponding pulse wave values or the ratio between corresponding pulse wave values.

Examples of the characteristic value that the blood pressure estimation unit 702 may calculate are described as Characteristic value 1 to Characteristic value 6 below. Specifically, the examples are:
- ratio between Pulse wave value 1 of the pulse wave signal 2001 and Pulse wave value 1 of the pulse wave signal 2002 . . . (Characteristic value 1)
- difference between Pulse wave value 2 of the pulse wave signal 2001 and Pulse wave value 2 of the pulse wave signal 2002 . . . (Characteristic value 2)
- difference between Pulse wave value 3 of the pulse wave signal 2001 and Pulse wave value 3 of the pulse wave signal 2002 . . . (Characteristic value 3)
- difference between Pulse wave value 4 of the pulse wave signal 2001 and Pulse wave value 4 of the pulse wave signal 2002 . . . (Characteristic value 4)
- ratio between Pulse wave value 5 of the pulse wave signal 2001 and Pulse wave value 5 of the pulse wave signal 2002 . . . (Characteristic value 5)
- difference between Pulse wave value 6 of the pulse wave signal 2001 and Pulse wave value 6 of the pulse wave signal 2002 . . . (Characteristic value 6).

The difference may be the absolute value of the difference. A difference to detect may be any difference as long as it represents the gap, such as ratio or difference. Accordingly, the characteristic value calculated by the blood pressure estimation unit 702 is not limited to the above-described examples.

In the following description, it is assumed, for convenience of description, the ratio regarding Characteristic value 1 is represented by, for example, (Pulse wave value 1 of the pulse wave signal 2001)/(Pulse wave value 1 of the pulse wave signal 2002) or (Pulse wave value 1 of the pulse wave signal 2002)/(Pulse wave value 1 of the pulse wave signal 2001).

Alternatively, it is assumed, for convenience of description, the ratio regarding Characteristic value 5 is represented by, for example, (Pulse wave value 5 of the pulse wave signal 2001)/(Pulse wave value 5 of the pulse wave signal 2002) or (Pulse wave value 5 of the pulse wave signal 2002)/(Pulse wave value 5 of the pulse wave signal 2001).

Subsequently, the blood pressure estimation unit 702 estimates blood pressure on the basis of the calculated characteristic value (Step S803).

Figure 10:
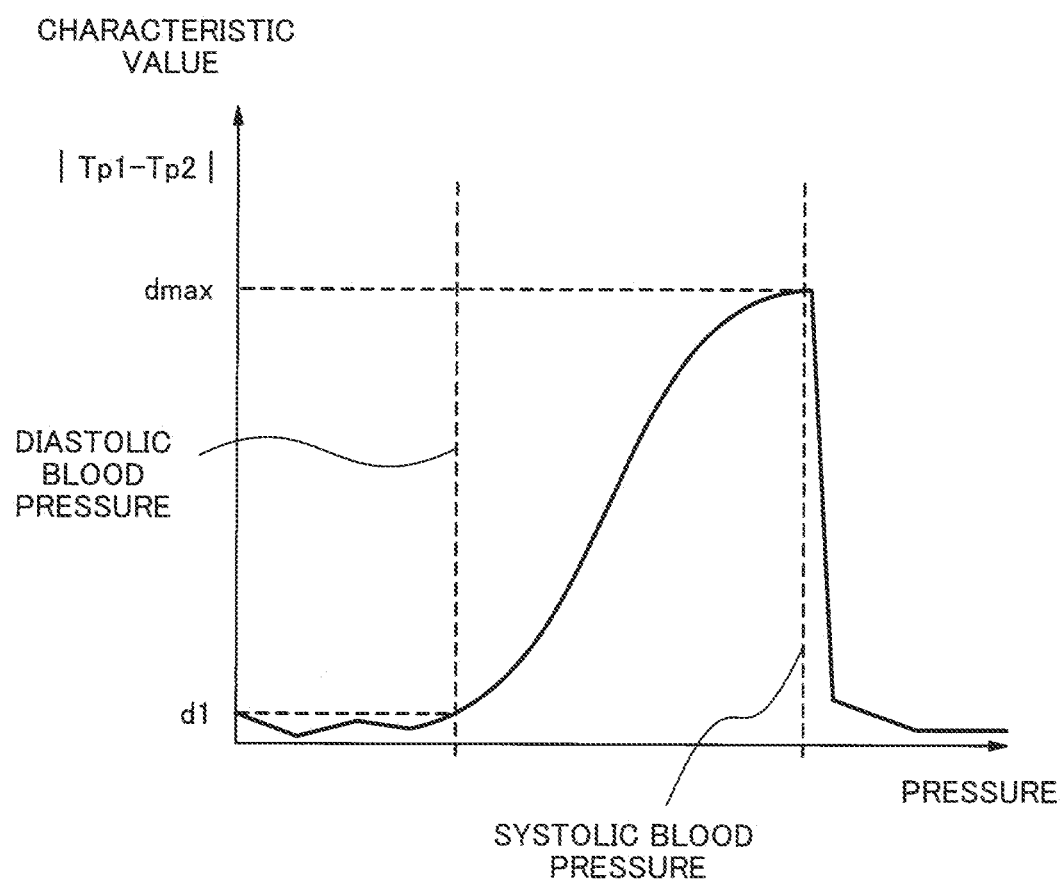
FIG. 10 is a graph illustrating an example of a relationship between a characteristic value and pressure.

The characteristic value changes according to the pressure being applied when pulse waves are measured. For example, Characteristic value 2 and pressure have a relationship as that presented in FIG. 10. FIG. 10 is a graph illustrating an example of a relationship between a characteristic value and pressure. The horizontal axis in FIG. 10 represents pressure indicated by the pressure signal 2003 and indicates a higher pressure at a rightward position. The vertical axis in FIG. 10 represents Characteristic value 2 and indicates larger Characteristic value 2 at a higher position. Characteristic value 2 starts to increase when the pressure is around the diastolic blood pressure and reaches the largest (or substantially largest) when the pressure is around the systolic blood pressure.

Each of Characteristic value 1 and Characteristic value 3 to Characteristic value 6 has a similar relationship between pressure and the characteristic value as that of Characteristic value 2.

For example, the blood pressure estimation unit 702 calculates a pressure having the largest (approximately the largest) difference in characteristic value, as a systolic blood pressure, and calculates a pressure having the difference in characteristic value smaller than a second certain value and being lower than the systolic blood pressure, as a diastolic blood pressure.

The blood pressure estimation device 701 according to the second exemplary embodiment has a configuration similar to that of the first exemplary embodiment and can hence obtain effects similar to those of the first exemplary embodiment. In other words, the blood pressure estimation device 701 according to the second exemplary embodiment can estimate blood pressure with a high degree of accuracy.

Movement of the subject to be measured, external vibrations, surrounding noise, and the like are added to pulse wave signals, as noise signals.

For convenience of description, measured signals including noise signals are denoted by $S_1$ and $S_2$, and pulse wave signals related to the subject to be measured are denoted by $P_1$ and $P_2$.

In this case, the measurement signals and the pulse wave signals have the relationships expressed by Equation 1 and Equation 2 below. Specifically, $$S_1 = P_1 \times a_1 + b_1 \quad \text{(Equation 1)}$$

$$S_2 = P_2 \times a_2 + b_2 \quad \text{(Equation 2)}$$

(where $a_1$ and $a_2$ respectively denote multiplication noise for the pulse wave signal $S_1$ and multiplication noise for the pulse wave signal $S_2$, and $b_1$ and $b_2$ respectively denote addition noise for the pulse wave signal $S_1$ and addition noise for the pulse wave signal $S_2$).

Here, k is defined according to Equation 3 below. Specifically, $$k = b_1/b_2 \quad \text{(Equation 3)}$$

Equation 4 below is established on the basis of Equation 1, Equation 2, and Equation 3 described above. Specifically, $$S_1 - k \times S_2 = P_1 \times a_1 - P_2 \times k \times a_2 \quad \text{(Equation 4)}$$

When $a_1$ and $a_2$ are sufficiently close to one (i.e., each multiplication noise is sufficiently small), or when a characteristic value that is not affected by any multiplication noise is extracted, $a_1$ and $a_2$ can be ignored, consequently reducing noise.

Here, m is defined according to Equation 5 below. Specifically, $$m = a_1/a_2 \quad \text{(Equation 5)}$$

Equation 6 below is established on the basis of Equation 1, Equation 2, and Equation 5 described above. Specifically, $$S_1/m/S_2 = (P_1 + b_1/a_1)/(P_2 + m \times b_2/a_1) \quad \text{(Equation 6)}$$

When $b_1$ and $b_2$ are sufficiently small with respect to $a_1$ and $a_2$, respectively, or when a characteristic value that is not affected by any addition noise is extracted, $a_1$ and $a_2$ can be ignored, consequently reducing noise.

Multiplication noise and addition noise are non-independently added to multiple pulse wave signals measured by multiple pulse wave measurement units located at positions close to each other. In this case, even when the values k and m are not determined, noise signal components can be reduced by calculating the difference.

Hence, the blood pressure estimation device 701 according to the second exemplary embodiment can estimate blood pressure with a high degree of accuracy.

Figure 11:
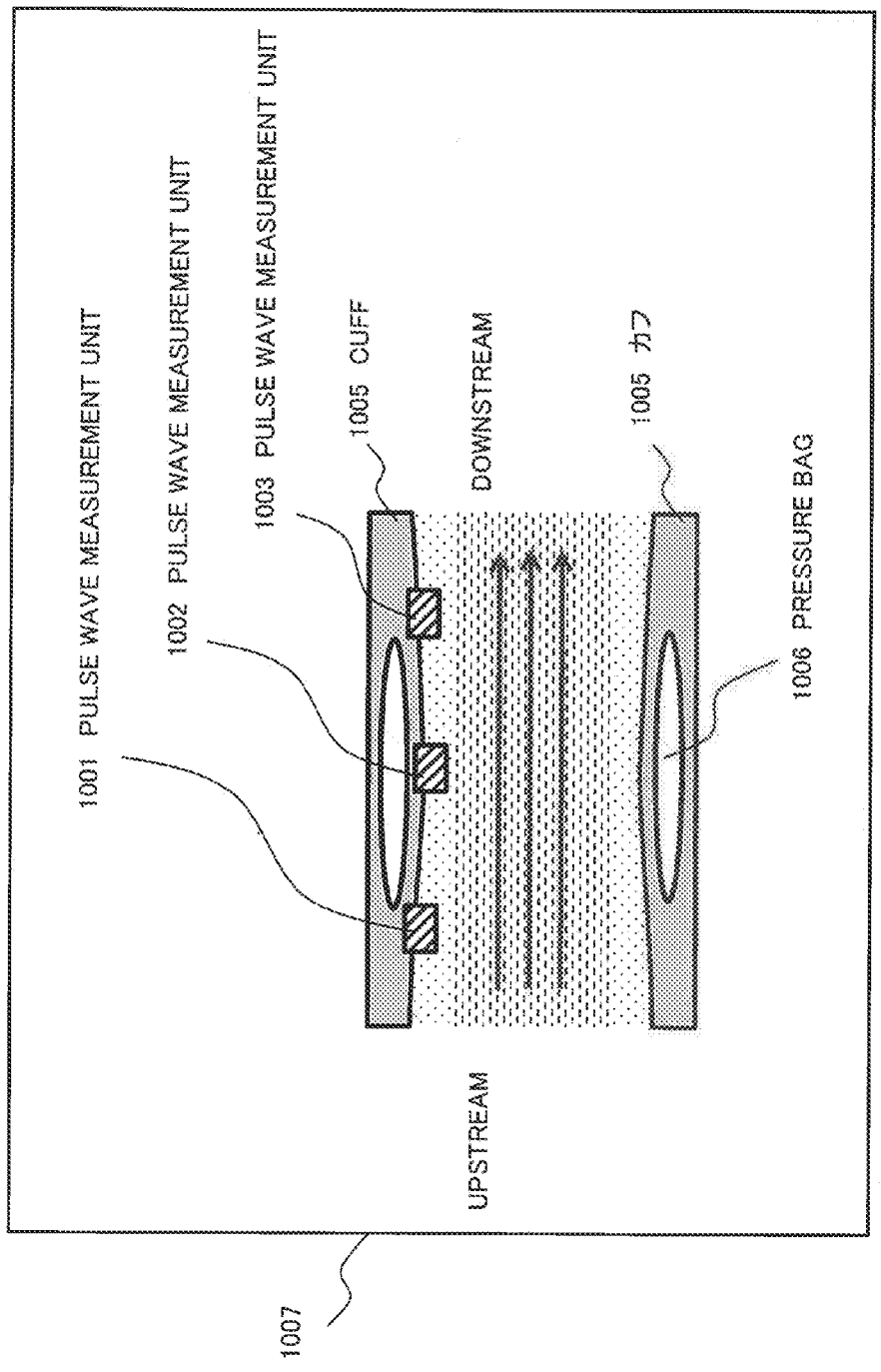
FIG. 11 is a diagram schematically illustrating a positional relationship between a cuff and three pulse wave measurement units.

When a blood pressure measurement device 1007 including the blood pressure estimation device 701 measures three pulse waves as illustrated in FIG. 11, the blood pressure estimation device 701 can also estimate blood pressure as the above-described example. FIG. 11 is a diagram schematically illustrating a positional relationship between a cuff 1005 and three pulse wave measurement units.

For convenience of description, FIG. 11 includes a specific region and a blood flow and the like in the specific region. However, the blood pressure measurement device 1007 does not include any specific region and any blood flow and the like in a specific region.

The blood pressure measurement device 1007 includes a pulse wave measurement unit 1001, a pulse wave measurement unit 1002, a pulse wave measurement unit 1003, and the cuff 1005. The cuff 1005 may include a pressure bag 1006. At least two pulse wave measurement units of the pulse wave measurement unit 1001, the pulse wave measurement unit 1002, and the pulse wave measurement unit 1003 are located at positions so that pressure center (or substantially center) in the shorter-side direction of the pressure application in the cuff 105 is located between the pulse wave measurement units.

Each of the pulse wave measurement unit 1001, the pulse wave measurement unit 1002, and the pulse wave measurement unit 1003 measures a pulse wave at the specific region.

Here, for convenience of description, measurement signals including noise are denoted by $S_1$, $S_2$, and $S_3$, and pulse signals are denoted by $P_1$, $P_2$, and $P_3$.

In this case, the measurement signals and the pulse wave signals have the relationships expressed by Equation 7 to Equation 9 below. Specifically, $$S_1 = P_1 \times a_1 + b_1 \quad \text{(Equation 7)}$$

$$S_2 = P_2 \times a_2 + b_2 \quad \text{(Equation 8)}$$

$$S_3 = P_3 \times a_3 + b_3 \quad \text{(Equation 9)}$$

(where $a_1$, $a_2$, and $a_3$ each denote multiplication noise for the corresponding pulse wave signal, and $b_1$, $b_2$, and $b_3$ each denote addition noise for the corresponding pulse wave signal).

Here, $k_1$ is defined according to Equation 10 below, and $k_2$ is defined according to Equation 11 below. Specifically, $$k_1 = b_1/b_2 \quad \text{(Equation 10)}$$

$$k_2 = b_1/b_3 \quad \text{(Equation 11)}$$

By calculating the difference between Equation 7 and Equation 8 and the difference between Equation 7 and Equation 9, Equation 12 and Equation 13 below are established. Specifically, $$S_1 - k_1 \times S_2 = P_1 \times a_1 - P_2 \times k_1 \times a_2 \quad \text{(Equation 12)}$$

$$S_1 - k_2 \times S_3 = P_1 \times a_1 - P_3 \times k_2 \times a_3 \quad \text{(Equation 13)}$$

By calculating (Equation 12) / (Equation 13), Equation 14 below is established. Specifically, $$(S_1 - k_1 \times S_2)/(S_1 - k_2 \times S_3) = (P_1 - P_2 \times k_1 \times a_2/a_1)/(P_1 - P_3 \times k_2 \times a_3/a_1) \quad \text{(Equation 14)}$$

Equation 14 indicates that, when $a_1$ is sufficiently close to $a_2$ and $a_3$ after the influences of the addition noises $b_1$, $b_2$, and $b_3$ are cancelled, the influences of the multiplication noises can be ignored. This indicates that noise can be reduced.

Further, the noise signals ($a_1$, $a_2$, $a_3$, $b_1$, $b_2$, and $b_3$) are non-independently added to multiple pulse signals measured by multiple pulse wave measurement units located at positions close to each other. Accordingly, Equation 14 indicates that the influences of these noises can be reduced by calculating the difference even when the values $k_1$ and $k_2$ are not determined.

Hence, the blood pressure estimation device 701 according to the second exemplary embodiment can reduce the influences of noise by estimating blood pressure on the basis of three or more pulse wave signals as described above.

Figure 12:
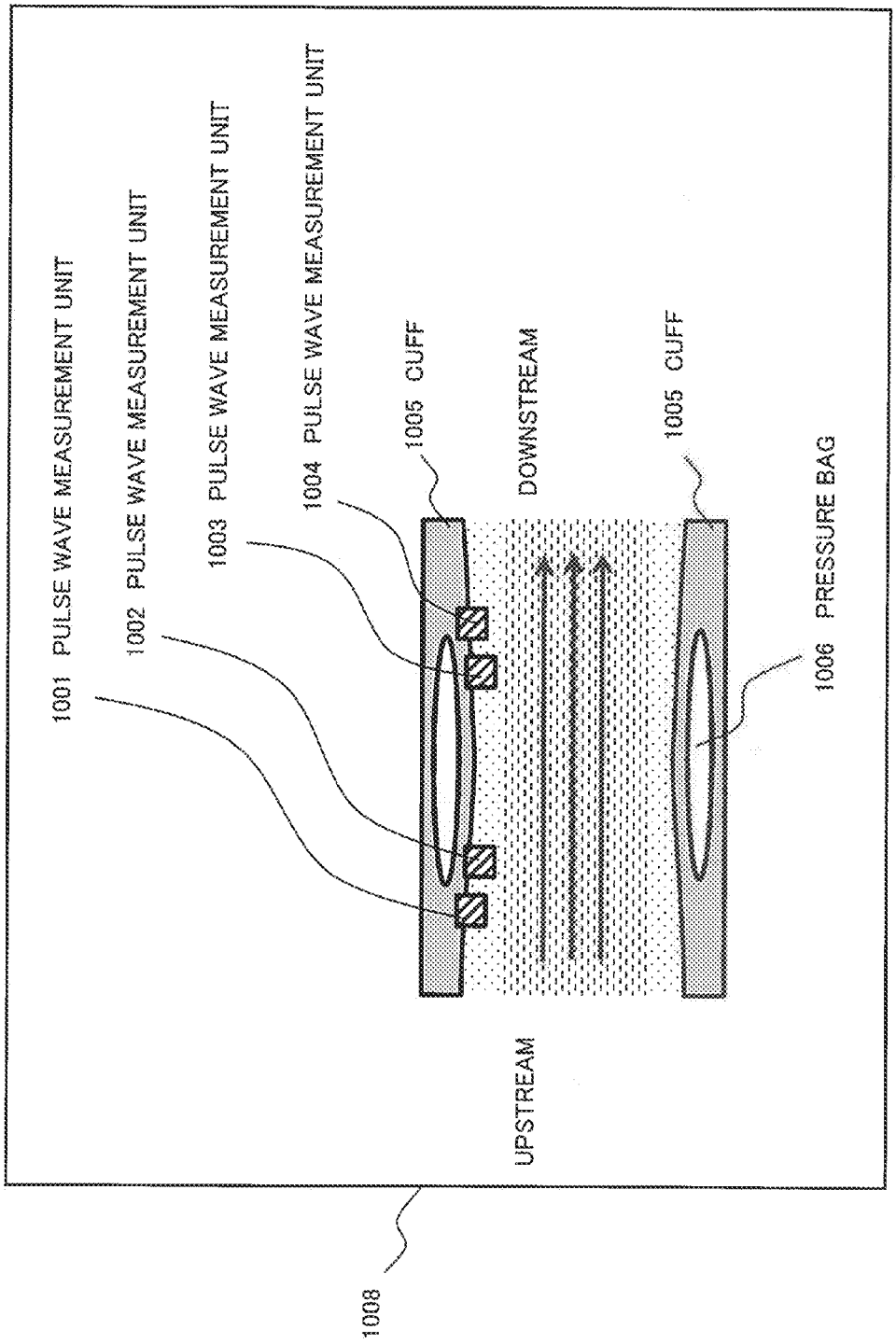
FIG. 12 is a diagram schematically illustrating a positional relationship between a cuff and four pulse wave measurement units.

When a blood pressure measurement device 1008 including the blood pressure estimation device 701 measures four pulse waves as illustrated in FIG. 12, the blood pressure estimation device 701 can also estimate blood pressure as the above-described example. FIG. 12 is a diagram schematically illustrating a positional relationship between a cuff and four pulse wave measurement units.

For convenience of description, FIG. 12 includes a specific region and a blood flow and the like in the specific region. However, the blood pressure measurement device 1008 does not include any specific region and any blood flow and the like in a specific region.

The blood pressure measurement device 1008 includes a pulse wave measurement unit 1001, a pulse wave measurement unit 1002, a pulse wave measurement unit 1003, a pulse wave measurement unit 1004, and a cuff 1005. The cuff 1005 may include a pressure bag 1006. At least two pulse wave measurement units of the pulse wave measurement unit 1001, the pulse wave measurement unit 1002, the pulse wave measurement unit 1003, and the pulse wave measurement unit 1004 are located at positions so that the pressure center (or substantially center) in the shorter-side direction of pressure application in the cuff 1005 is located between the pulse wave measurement units.

Each of the pulse wave measurement unit 1001, the pulse wave measurement unit 1002, the pulse wave measurement unit 1003, and the pulse wave measurement unit 1004 measures a pulse wave at the specific region.

The blood pressure estimation device 701 estimates blood pressure on the basis of the pulse wave measurement unit 1001, the pulse wave measurement unit 1002, the pulse wave measurement unit 1003, and the pulse wave measurement unit 1004 as in the above-described process.

Hence, the blood pressure estimation device according to the second exemplary embodiment can reduce the influence of noise by estimating blood pressure on the basis of four or more pulse wave signals, based on reasons similar to those described above.

<Third Exemplary Embodiment>

Next, a third exemplary embodiment of the present invention based on the above-described first exemplary embodiment will be described.

In the following description, characteristic parts of the present exemplary embodiment will be mainly described, and the same components as in the above-described first exemplary embodiment are assigned with the same reference signs, whereby overlapping description will be omitted.

Figure 13:
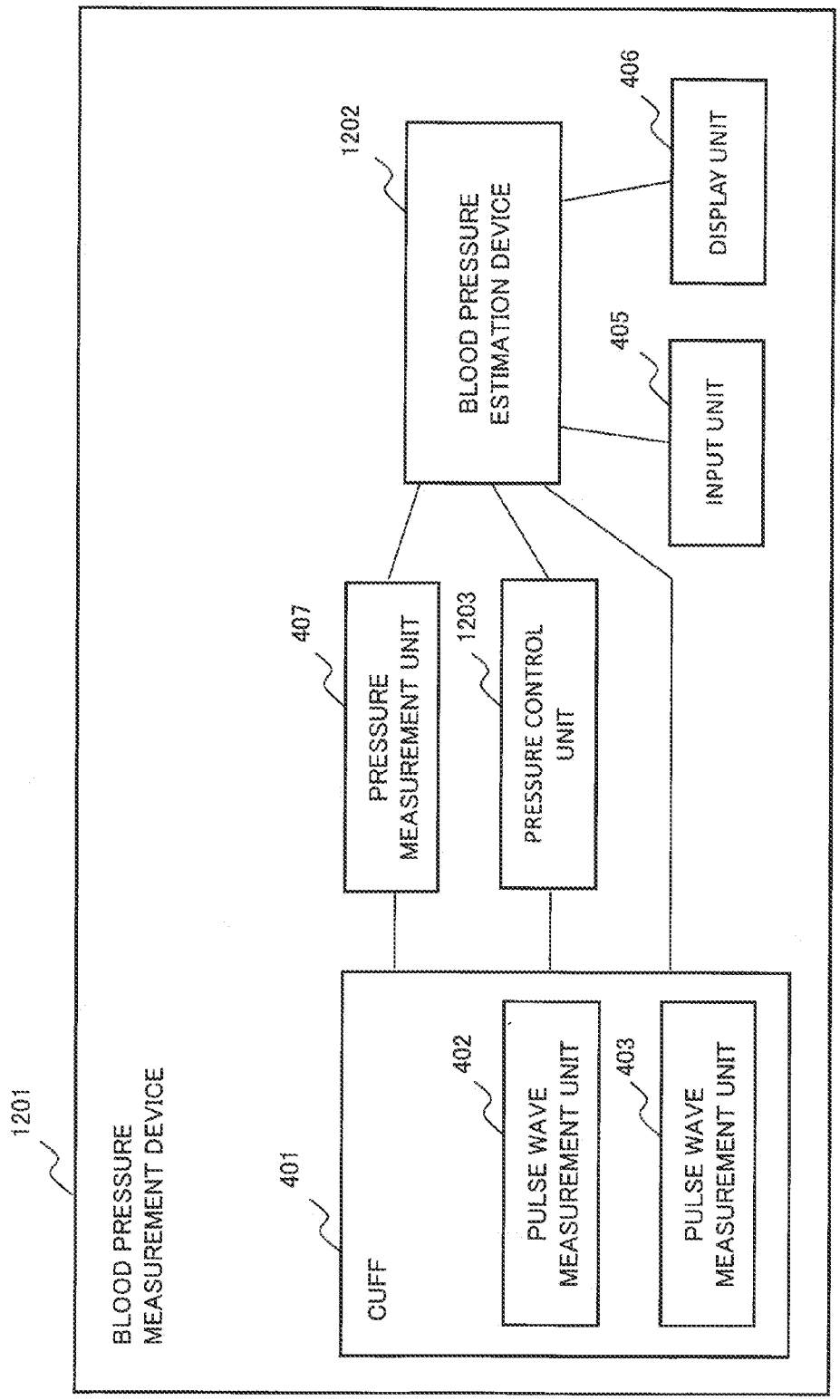
FIG. 13 is a block diagram illustrating a configuration of a blood pressure estimation device according to a third exemplary embodiment of the present invention.
Figure 14:
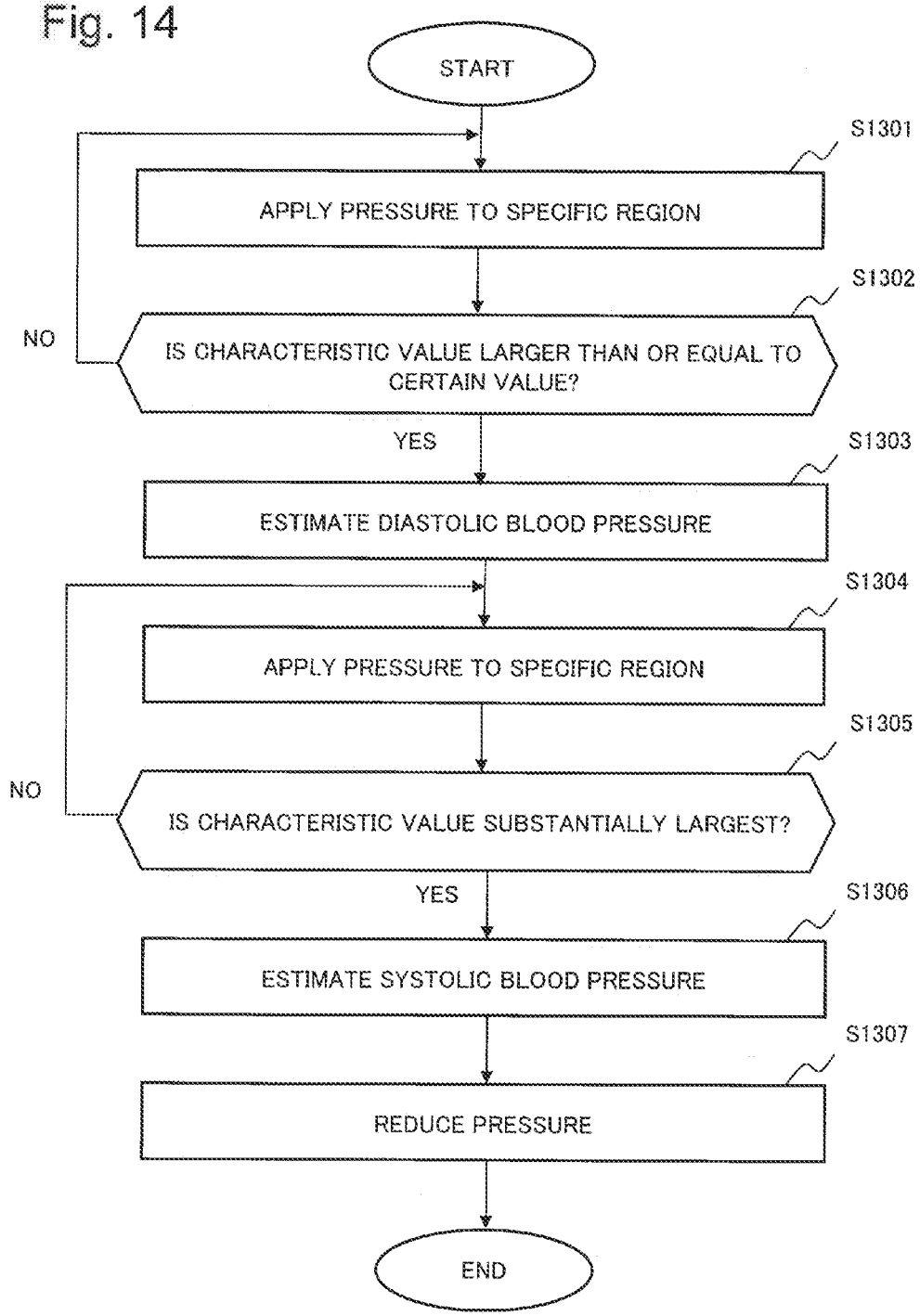
FIG. 14 is a flowchart presenting flow of processes by a blood pressure estimation device according to the third exemplary embodiment.

With reference to FIG. 13 and FIG. 14, description will be given of a configuration of a blood pressure estimation device 1201 according to the third exemplary embodiment and a processing executed by the blood pressure estimation device 1201. FIG. 13 is a block diagram illustrating the configuration of the blood pressure estimation device 1201 according to the third exemplary embodiment of the present invention. FIG. 14 is a flowchart presenting the flow of the process by the blood pressure estimation device 1201 according to the third exemplary embodiment.

The blood pressure measurement device 1201 includes a cuff 401, a pulse wave measurement unit 402, a pulse wave measurement unit 403, a pressure measurement unit 407, a pressure control unit 1203, an input unit 405, a display unit 406, and a blood pressure estimation device 1202.

First, when measurement is started, the pressure control unit 1203 performs control so as to increase the internal pressure of the cuff 401 (Step S1301). In the process of applying pressure, the pressure measurement unit 407 measures the internal pressure of the cuff 401 and transmits the measured pressure as a pressure signal 2003 to the blood pressure estimation device 1202. The pulse wave measurement unit 402 and the pulse wave measurement unit 403 measure pulse waves at a specific region and transmits the measured pulse waves as pulse wave signals (i.e., a pulse wave signal 2001 and a pulse wave signal 2002) to the blood pressure estimation device 1202.

Subsequently, the blood pressure estimation device 1202 receives the pressure signal 2003 and the pulse wave signals and calculates a characteristic value on the basis of the received pressure signal 2003 and pulse wave signals. The blood pressure estimation device 1202 then determines whether the calculated characteristic value is larger than or equal to a predetermined value (Step S1302).

When determining that the characteristic value is larger than or equal to the predetermined value (Yes in Step S1302), the blood pressure estimation device 1202 calculates the pressure indicated by the pressure signal 2003, as a diastolic blood pressure (Step S1303). When determining that the characteristic value is smaller than the predetermined value (No in Step S1302), the blood pressure estimation device 1202 transmits a control signal for increasing pressure to the pressure control unit 1203. Upon receipt of the control signal, the pressure control unit 1203 performs control so as to increase the internal pressure of the cuff 401 according to the received control signal (Step S1301).

After calculating the diastolic blood pressure, the blood pressure estimation device 1202 transmits a control signal for increasing pressure to the pressure control unit 1203. Upon receipt of the control signal, the pressure control unit 1203 performs control so as to increase the internal pressure of the cuff 401 according to the received control signal (Step S1304).

Subsequently, the blood pressure estimation device 1202 receives the pressure signal 2003 and pulse wave signals after the pressure application and calculates a characteristic value on the basis of the received pressure signal 2003 and pulse wave signals. The blood pressure estimation device 1202 then determines whether the calculated characteristic value is the largest (approximately the largest) (Step S1305).

When determining that the characteristic value is the largest (or approximately the largest) (Yes in Step S1305), the blood pressure estimation device 1202 estimates the pressure indicated by the pressure signal 2003 as a systolic blood pressure (Step S1306). When determining that the characteristic value is not the largest (or approximately the largest) (No in Step S1305), the blood pressure estimation device 1202 transmits a control signal for increasing pressure to the pressure control unit 1203. Upon receipt of the control signal, the pressure control unit 1203 performs control so as to increase the internal pressure of the cuff 401 according to the received control signal (Step S1304).

After calculating the systolic blood pressure, the blood pressure estimation device 1202 transmits a second control signal for decreasing pressure to the pressure control unit 1203. Upon receipt of the second control signal, the pressure control unit 1203 performs control to reduce the internal pressure of the cuff 401 according to the received second control signal (Step S1307).

The blood pressure measurement device 1201 according to the third exemplary embodiment has a configuration similar to that of the first exemplary embodiment and can hence obtain effects similar to those of the first exemplary embodiment. In other words, the blood pressure measurement device 1201 according to the third exemplary embodiment can estimate blood pressure with a high degree of accuracy.

The blood pressure measurement device 1201 estimates a systolic blood pressure by applying pressure around the systolic blood pressure while increasing the internal pressure of the cuff 401. In contrast, common blood pressure measurement devices estimate a systolic blood pressure while reducing the internal pressure of the cuff 401 after applying pressure to reach a blood pressure sufficiently higher than a systolic blood pressure.

Hence, the blood pressure measurement device 1201 according to this exemplary embodiment can estimate a systolic blood pressure with a pressure lower than those used by common blood pressure measurement devices.

In other words, with the blood pressure measurement device 1201 according to this exemplary embodiment, it is possible to reduce measurement time and also reduce burden on the subject to be measured.

<Fourth Exemplary Embodiment>

Next, a fourth exemplary embodiment of the present invention based on the above-described third exemplary embodiment will be described.

In the following description, the characteristic parts of the present exemplary embodiment are mainly described, and the same components as in the above-described third exemplary embodiment are assigned with the same reference signs, whereby overlapping description will be omitted.

Figure 15:
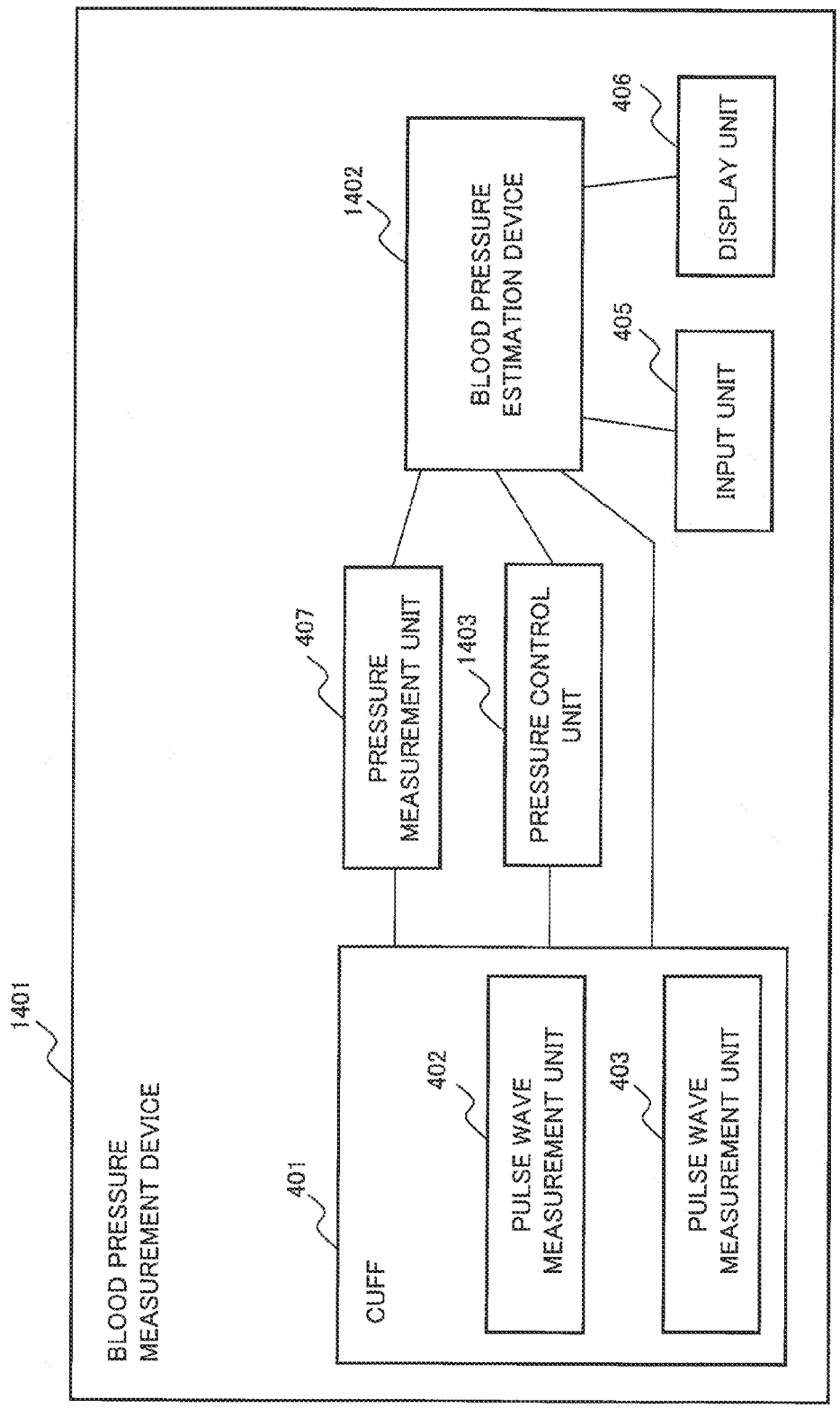
FIG. 15 is a block diagram illustrating a configuration of a blood pressure measurement device according to a fourth exemplary embodiment of the present invention.
Figure 16:
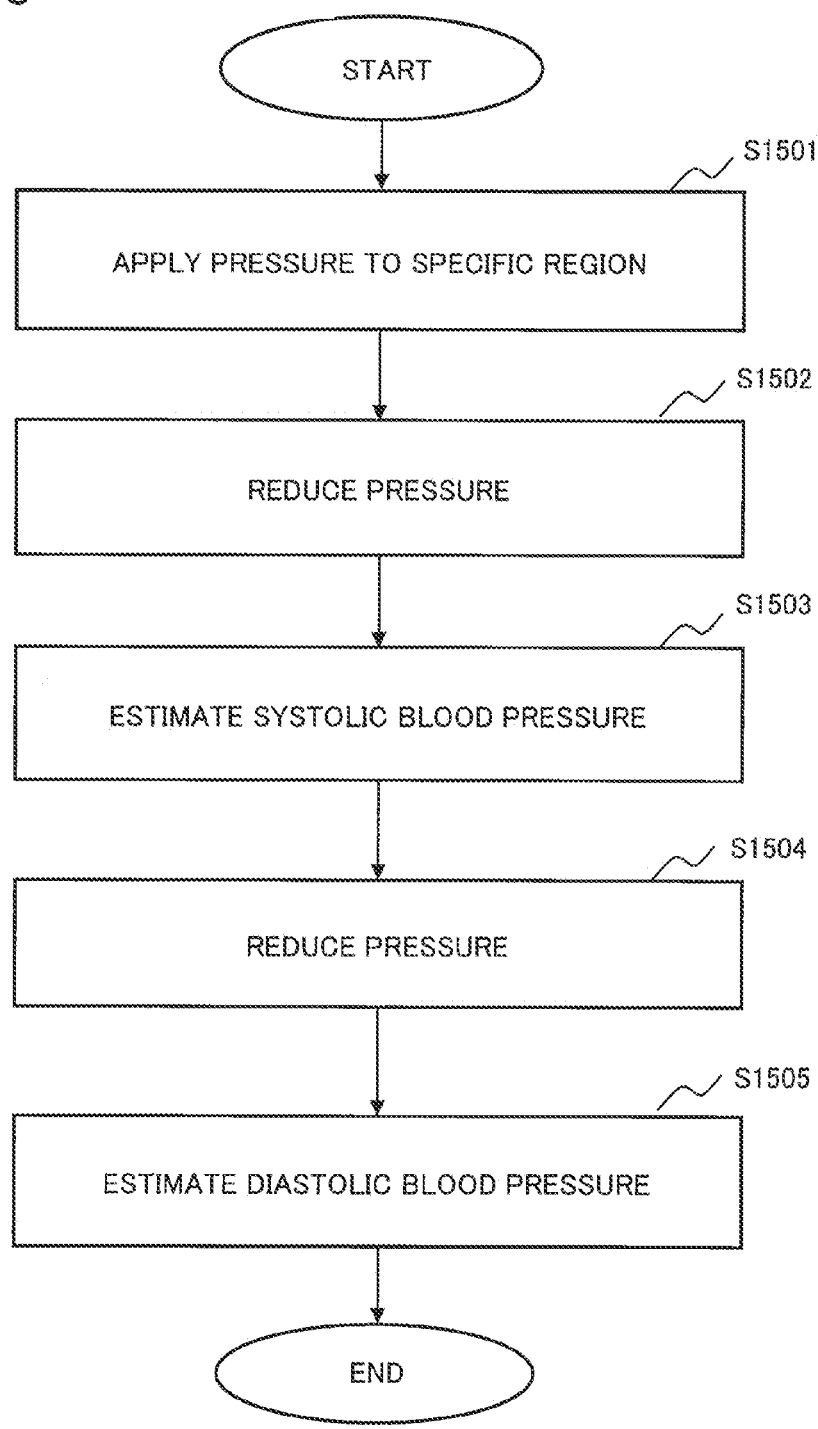
FIG. 16 is a flowchart presenting a flow of processes by the blood pressure measurement device according to the fourth exemplary embodiment.

With reference to FIG. 15 and FIG. 16, description will be given of a configuration of a blood pressure measurement device 1401 according to the fourth exemplary embodiment and a processing executed by the blood pressure measurement device 1401. FIG. 15 is a block diagram illustrating the configuration of the blood pressure measurement device 1401 according to the fourth exemplary embodiment of the present invention. FIG. 16 is a flowchart presenting the flow of the process by the blood pressure measurement device 1401 according to the fourth exemplary embodiment.

The blood pressure measurement device 1401 includes a cuff 401, a pulse wave measurement unit 402, a pulse wave measurement unit 403, a pressure measurement unit 407, a pressure control unit 1403, an input unit 405, a display unit 406, and a blood pressure estimation device 1402.

First, when a subject to be measured starts measurement, the pressure control unit 1403 performs control so as to increase the internal pressure of the cuff 401 to a predetermined pressure (pressure sufficiently higher than a normal systolic blood pressure) (Step S1501). The pressure control unit 1403 then performs control so as to reduce the pressure (Step S1502). In the course of the pressure being reduced, the pressure measurement unit 407 measures the internal pressure of the cuff 401 and transmits the measured pressure as a pressure signal 2003 to the blood pressure estimation device 1402. The pulse wave measurement unit 402 and the pulse wave measurement unit 403 measure pulse waves at a specific region and transmits the measured pulse waves as pulse wave signals to the blood pressure estimation device 1402.

In this exemplary embodiment, the pulse wave measurement unit 402 and the pulse wave measurement unit 403 are vibration sensors that detect vibrations arising from pulse waves.

Figure 17A:
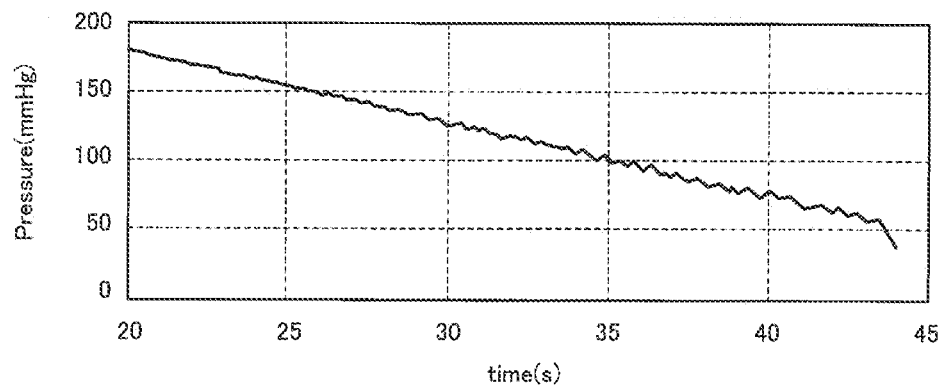
FIG. 17A is a graph presenting an example of pressure measured by a pressure measurement unit.
Figure 17B:
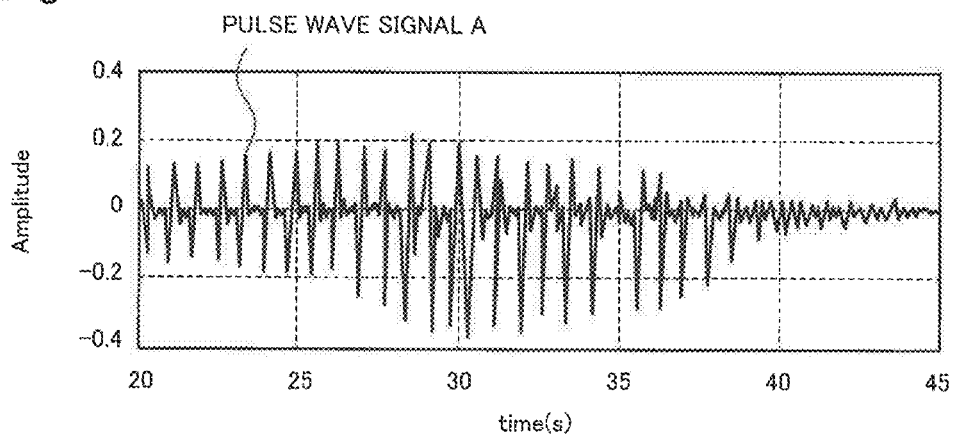
FIG. 17B is a graph presenting an example of a pulse wave measured by a pulse wave measurement unit.
Figure 17C:
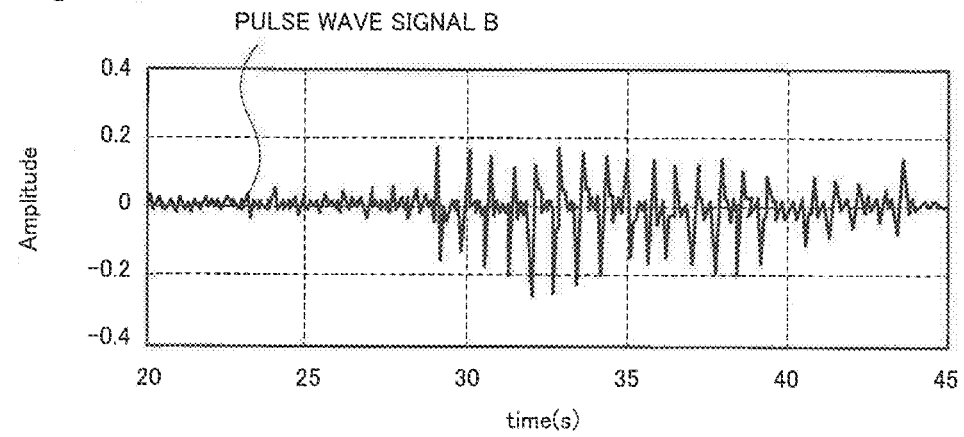
FIG. 17C is a graph presenting an example of a pulse wave measured by a pulse wave measurement unit.

The pressure measurement unit 407, the pulse wave measurement unit 402, and the pulse wave measurement unit 403 each measure the pressure and the pulse wave presented in a corresponding one of FIG. 17A to FIG. 17C. FIG. 17A is a graph presenting an example of pressure measured by the pressure measurement unit 407. FIG. 17B is a graph presenting an example of a pulse wave measured by the pulse wave measurement unit 402 (referred to as "pulse wave signal A" below). FIG. 17C is a graph presenting an example of a pulse wave measured by the pulse wave measurement unit 403 (referred to as "pulse wave signal B" below). The horizontal axis in each of FIG. 17A to FIG. 17C represents time and indicates a later time at a rightward position. The vertical axis in FIG. 17A represents pressure and indicates a higher pressure at a higher position. The vertical axis in each of FIG. 17B and FIG. 17C represents the amplitude of the corresponding pulse wave and indicates a larger amplitude at a higher or lower position and a smaller amplitude at a position closer to zero.

Since the pressure control unit 1403 performs control in Step S1501 and Step S1502, the pressure decreases with time (FIG. 17A).

Figure 18A:
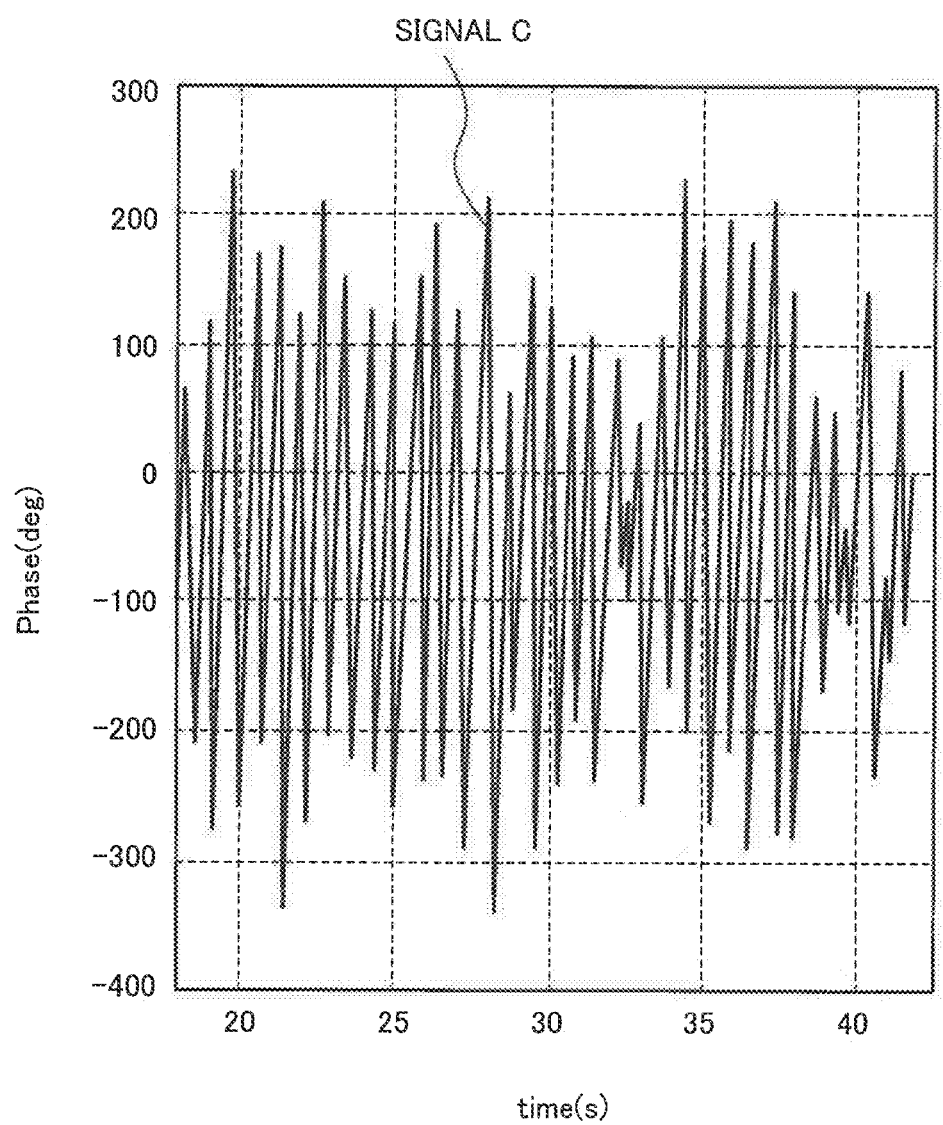
FIG. 18A is a graph each presenting an example of a signal obtained by calculating Fourier transform of a pulse wave.
Figure 18B:
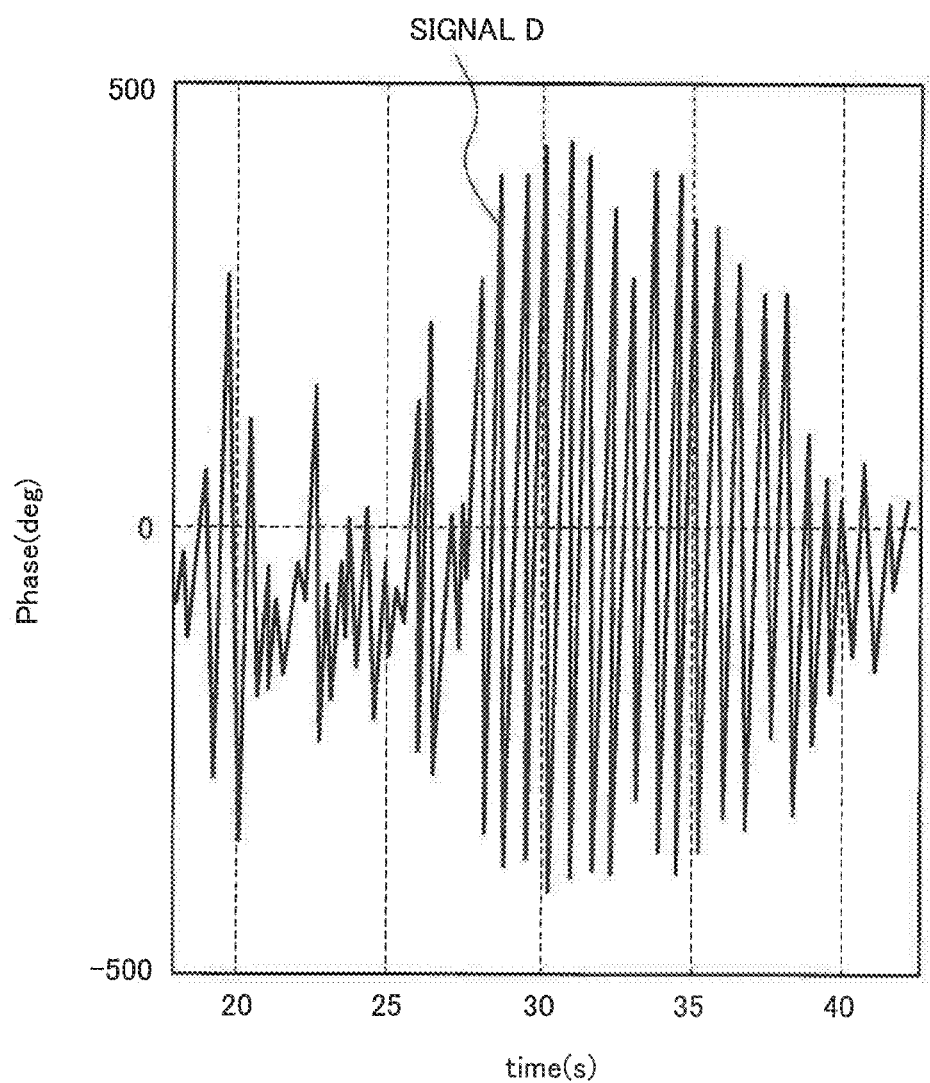
FIG. 18B is a graph each presenting an example of a signal obtained by calculating Fourier transform of a pulse wave.

The blood pressure estimation device 1402 receives a pulse wave signal A and a pulse wave signal B and calculates short-time Fourier transform of each of the received pulse wave signals. In this exemplary embodiment, it is assumed that Fourier transform is performed on a pulse wave corresponding to a single heartbeat. In this case, the blood pressure estimation device 1402 calculates Fourier transform of the pulse wave signal A to thereby calculate a signal C presented in FIG. 18A. Similarly, the blood pressure estimation device 1402 calculates Fourier transform of the pulse wave signal B to thereby calculate a signal D presented in FIG. 18B. FIG. 18A and FIG. 18B are graphs each presenting an example of a signal obtained by calculating Fourier transform of a pulse wave.

Figure 19:
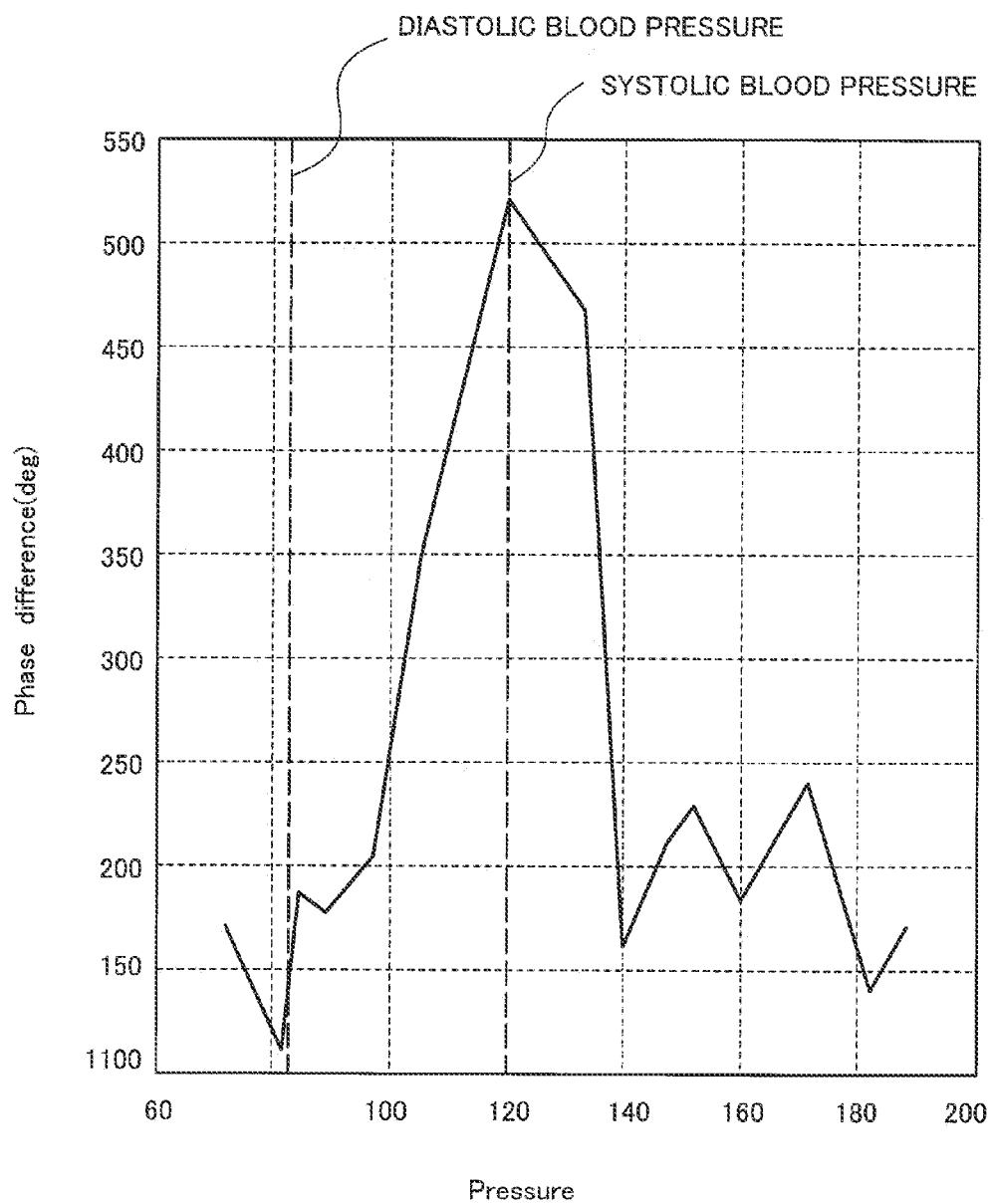
FIG. 19 is a graph presenting an example of a relationship between a characteristic value and pressure.

The blood pressure estimation device 1402 then calculates a pulse wave value described as a pulse wave value 6 and calculates a characteristic value 6 as illustrated in FIG. 19 on the basis of the calculated pulse wave value. FIG. 19 is a graph presenting an example of a relationship between a characteristic value and pressure. The horizontal axis in FIG. 19 represents a pressure indicated by the pressure signal 2003 and indicates a higher pressure at a rightward position. The vertical axis in FIG. 19 represents Characteristic value 6 and indicates larger Characteristic value 6 at a higher position. Characteristic value 6 starts to increase from where the pressure is around the diastolic blood pressure and reaches the local maximum where the pressure is around the systolic blood pressure.

The blood pressure estimation device 1402 estimates the pressure having the local maximum (or substantially local maximum) difference in characteristic value, as a systolic blood pressure (Step S1503) and estimates a pressure having the difference in characteristic value that is smaller than a second certain value and being smaller than the systolic blood pressure, as a diastolic blood pressure (Step S1505). In this case, the pressure control unit 1403 continues the control so as to reduce the pressure (Step S1504).

The blood pressure measurement device 1401 according to the fourth exemplary embodiment has a configuration similar to that of the first exemplary embodiment and can hence obtain effects similar to those of the first exemplary embodiment. In other words, the blood pressure estimation device 1401 according to the fourth exemplary embodiment can estimate blood pressure with a high degree of accuracy.

The blood pressure measurement device 1401 estimates blood pressure by measuring pulse waves in the course of reducing pressure after sufficiently applying pressure. As a result, the blood pressure measurement device 1401 according to this exemplary embodiment can measure pulse waves of pressure in a larger range, and can hence estimate blood pressure with a higher degree of accuracy.

The blood pressure measurement device 1401 does not need to estimate blood pressure only in the course of applying pressure or the course of decreasing pressure as described in the third exemplary embodiment and the fourth exemplary embodiment. The blood pressure measurement device 1401 may control pressure on the basis of a characteristic value calculated by the blood pressure estimation device 1402.

For example, when a characteristic value decreases as the internal pressure of the cuff 401 is reduced, the pressure is lower than the systolic blood pressure, and accordingly the pressure control unit 1403 may perform control so as to increase the internal pressure of the cuff 401. In contrast, when the characteristic value does not decrease although the internal pressure of the cuff 401 is reduced, the pressure is higher than the systolic blood pressure, and accordingly the pressure control unit 1403 may perform control so as to reduce the internal pressure of the cuff 401. In this case, the blood pressure estimation device 1402 estimates a systolic blood pressure while the pressure control unit 1403 repeats increasing and decreasing of pressure. Thereafter, while reducing the internal pressure of the cuff 401, the blood pressure measurement device 1401 estimates the pressure having the characteristic value smaller than or equal to a predetermined value, as a diastolic blood pressure.

When the above-described processing is executed, it is possible to find a systolic blood pressure by repeating the process of applying pressure and the process of reducing pressure. Hence, the blood pressure measurement device 1401 can estimate blood pressure with a higher degree of accuracy.

Further, the blood pressure measurement device 1401 may estimate blood pressure in the course of applying pressure and also estimate blood pressure in the course of reducing pressure. In this case, the blood pressure measurement device 1401 estimates blood pressure by, for example, averaging the two blood pressures.

Alternatively, the blood pressure measurement device 1401 may estimate blood pressure in two processes while repeating the process of applying pressure and the process of reducing pressure. In this case, the blood pressure measurement device 1401 estimates blood pressure by, for example, averaging the blood pressures measured in each process.

When the above-described processing is executed, the estimated blood pressure is more accurate by, for example, averaging the blood pressures calculated in the course of repeating application and reduction of pressure. Hence, the blood pressure measurement device 1401 can estimate blood pressure with a higher degree of accuracy.

(Hardware Configuration Example)

A configuration example of hardware resources that realize a blood pressure estimation device in the above-described exemplary embodiments of the present invention using a single calculation processing apparatus (an information processing apparatus or a computer) will be described. However, the pressure estimation device may be realized using physically or functionally at least two calculation processing apparatuses. Further, the pressure estimation device may be realized as a dedicated apparatus.

Figure 20:
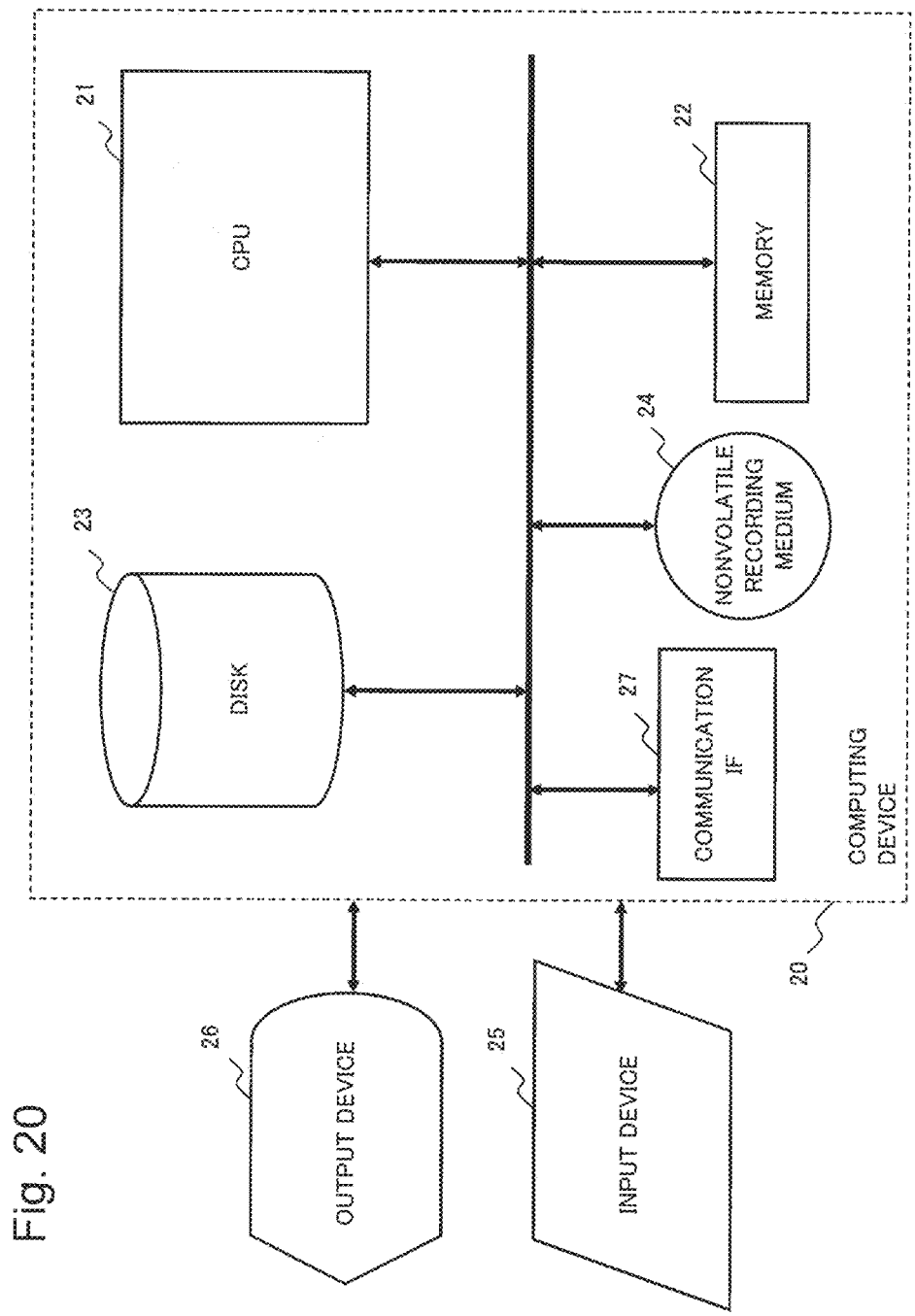
FIG. 20 is a block diagram schematically illustrating a hardware configuration of a calculation processing apparatus capable of realizing a blood pressure estimation device or a pressure controlling unit Description of Embodiments according to each exemplary embodiment.

FIG. 20 is a block diagram schematically illustrating a hardware configuration of a calculation processing apparatus capable of realizing the blood pressure estimation device according to each of the first exemplary embodiment to the four exemplary embodiment or a pressure controlling unit in the blood pressure measurement device. A calculation processing apparatus 20 includes a central processing unit (CPU) 21, a memory 22, a disc 23, a non-transitory recording medium 24, an input apparatus 25, an output apparatus 26, and a communication interface (hereinafter, expressed as a "communication I/F") 27. The calculation processing apparatus 20 can execute transmission/reception of information to/from another calculation processing apparatus and a communication apparatus via the communication I/F 27.

The non-transitory recording medium 24 is, for example, a computer-readable Compact Disc, Digital_Versatile_Disc. The non-transitory recording medium 24 is, for example, Universal Serial Bus (USB) memory, or Solid State Drive. The non-transitory recording medium 24 allows a related program to be holdable and portable without power supply. The non-transitory recording medium 24 is not limited to the above-described media. Further, a related program can be carried via a communication network by way of the communication I/F 27 instead of the non-transitory medium 24.

In other words, the CPU 21 copies, on the memory 22, a software program (a computer program: hereinafter, referred to simply as a "program") stored by the disc 23 when executing the program and executes arithmetic processing. The CPU 21 reads data necessary for program execution from the memory 22. When display is needed, the CPU 21 displays an output result on the output apparatus 26. When a program is input from the outside, the CPU 21 reads the program from the input apparatus 25. The CPU 21 interprets and executes a blood pressure estimation program present on the memory 22 corresponding to a function (processing) indicated by each unit illustrated in FIG. 1, FIG. 4, FIG. 8, FIG. 13, or FIG. 15 described above or an blood pressure estimation program (FIG. 2, FIG. 9, FIG. 14, or FIG. 16). The CPU 21 sequentially executes the processing described in each exemplary embodiment of the present invention.

In other words, in such a case, it is conceivable that the present invention can also be made using the blood pressure estimation program. Further, it is conceivable that the present invention can also be made using a computer-readable, non-transitory recording medium storing the blood pressure estimation program.

Part of or the entire of each of the above-described exemplary embodiments may be described as the following supplementary notes. However, the present invention illustrated by the use of the above-described exemplary embodiments is not limited to the following. The supplementary notes are as follows.

(Supplementary Note 1)

A blood pressure estimation device including blood pressure estimation means for estimating a blood pressure on the basis of a pressure in a certain time period and difference between a plurality of pulse wave signals measured in association with the pressure.

(Supplementary Note 2)

The blood pressure estimation device according to Supplementary Note 1, wherein the blood pressure estimation means calculates a pulse wave value representing the plurality of pulse wave signals when the plurality of pulse wave signals satisfy a predetermined condition, and estimates the blood pressure on the basis of difference between the pulse wave values calculated for the plurality of pulse wave signals.

(Supplementary Note 3)

The blood pressure estimation device according to Supplementary Note 1 or Supplementary Note 2, wherein the pulse wave values is a phase obtained by frequency space transformation of the corresponding pulse wave signal, and the difference is difference between the phases of the plurality of pulse wave signals.

(Supplementary Note 4)

The blood pressure estimation device according to Supplementary Note 1 or Supplementary Note 2, wherein the pulse wave value is an amplitude obtained by frequency space transformation of the corresponding pulse wave signal, and the difference is a ratio between the amplitudes of the plurality of pulse wave signals.

(Supplementary Note 5)

The blood pressure estimation device according to Supplementary Note 1 or Supplementary Note 2, wherein the pulse wave value is a timing at which the corresponding pulse wave signal reaches an extremum or an approximate extremum in a single heartbeat, and the difference is difference between the timings of the plurality of pulse wave signals.

(Supplementary Note 6)

The blood pressure estimation device according to Supplementary Note 1 or Supplementary Note 2, wherein the pulse wave value is an amplitude obtained when the corresponding pulse wave signal reaches an extremum or an approximate extremum in a single heartbeat, and the difference is a ratio between the amplitudes of the plurality of pulse wave signals.

(Supplementary Note 8)

The blood pressure estimation device according to any one of Supplementary Note 1 to Supplementary Note 7, wherein the blood pressure estimation means estimates a pressure obtained when the difference is largest or around the largest as a systolic blood pressure.

(Supplementary Note 9)

The blood pressure estimation device according to any one of Supplementary Note 1 to Supplementary Note 7, wherein the blood pressure estimation means estimates a pressure that is lower than that obtained when the difference is largest or around the largest and that has the difference smaller than or equal to a predetermined value, as a diastolic blood pressure.

(Supplementary Note 10)

A blood pressure measurement device including the blood pressure estimation device according to any one of Supplementary Note 1 to Supplementary Note 9, wherein the blood pressure estimation device estimates a blood pressure in a course of a pressure being applied to a cuff.

(Supplementary Note 11)

The blood pressure measurement device including:

the blood pressure estimation device according to any one of Supplementary Note 1 to Supplementary Note 9; and pressure control means for controlling internal pressure of a cuff according to the difference.

(Supplementary Note 12)

The blood pressure measurement device according to Supplementary Note 10 or Supplementary Note 11, further including:

first pulse wave measurement means for measuring a pulse wave at upstream of an artery in the certain time period in association with a certain pressure, and transmitting the measured pulse wave as the pulse wave signal to the blood pressure estimation device; and second pulse wave measurement means for measuring the pulse wave at downstream of the artery in the certain time period in association with the certain pressure, and transmitting the measured pulse wave as the pulse wave signal to the blood pressure estimation device, wherein the blood pressure estimation device receives the pulse wave signal transmitted by the first pulse wave measurement means and the pulse wave signal transmitted by the second pulse wave measurement means, and estimates the blood pressure on the basis of the two received pulse wave signals.

(Supplementary Note 13)

The blood pressure measurement device according to Supplementary Note 12, wherein the first pulse wave measurement means and the second pulse wave measurement means are arranged so that a shorter-side direction center or a substantially shorter-side direction center of pressure application in the cuff is located between the first pulse wave measurement means and the second pulse wave measurement means.

(Supplementary Note 14)

The blood pressure measurement device according to Supplementary Note 12 or Supplementary Note 13, wherein the first pulse wave measurement means or the second pulse wave measurement means is a vibration sensor that detects vibration.

(Supplementary Note 15)

The blood pressure measurement device according to any one of Supplementary Note 12 to Supplementary Note 14, wherein the first pulse wave measurement means or the second pulse wave measurement means is a photoelectric sensor that detects reflected light obtained when light is applied to a specific region or transmitted light obtained when light is applied to a specific region.

(Supplementary Note 16)

The blood pressure measurement device according to any one of Supplementary Note 12 to Supplementary Note 15, wherein the first pulse wave measurement means or the second pulse wave measurement means is a pressure sensor that measures a pressure.

(Supplementary Note 17)

The blood pressure measurement device according to any one of Supplementary Note 10 to Supplementary Note 16, further including:

first pulse wave measurement means for measuring a pulse wave at upstream of an artery in the certain time period in association with a certain pressure, and transmitting the measured pulse wave as the pulse wave signal to the blood pressure estimation device; and second pulse wave measurement means for measuring a pulse wave at downstream of the artery in the certain time period in association with the certain pressure, and transmitting the measured pulse wave as the pulse wave signal to the blood pressure estimation device, wherein the blood pressure estimation device receives the pulse wave signal transmitted by the first pulse wave measurement means and the pulse wave signal transmitted by the second pulse wave measurement means, and estimates the blood pressure on the basis of the two received pulse wave signals (Supplementary Note 19)

A blood pressure estimation method including; estimating, by using an information processing device, a blood pressure on the basis of a pressure in a certain time period and difference between a plurality of pulse wave signals measured in association with the pressure in the certain time period.

(Supplementary Note 20)

A recording medium that records a blood pressure estimation program for causing a computer to implement a blood pressure estimation function of estimating a blood pressure on the basis of a pressure in a certain time period and difference between a plurality of pulse wave signals measured in association with the pressure in the certain time period.

The present invention has been described using the above-described exemplary embodiments as exemplary cases. However, the present invention is not limited to the above-described exemplary embodiments. In other words, the present invention is applicable with various aspects that can be understood by those skilled in the art without departing from the scope of the present invention.

This application is based upon and claims the benefit of priority from Japanese patent application No. 2014-025371, filed on Feb. 13, 2014, the disclosure of which is incorporated herein in its entirety.

REFERENCE SIGNS LIST

101 Blood pressure estimation device
102 Blood pressure estimation unit
2001 Pulse wave signal
2002 Pulse wave signal
2003 Pressure signal
401 Cuff
402 Pulse wave measurement unit
403 Pulse wave measurement unit
404 Pressure control unit
405 Input unit
406 Display unit
407 Pressure measurement unit
408 Blood pressure measurement device
701 Blood pressure estimation device
702 Blood pressure estimation unit
1001 Pulse wave measurement unit
1002 Pulse wave measurement unit
1003 Pulse wave measurement unit
1004 Pulse wave measurement unit
1005 Cuff
1006 Pressure bag
1007 Blood pressure measurement device
1008 Blood pressure measurement device
1201 Blood pressure measurement device
1202 Blood pressure estimation device
1203 Pressure control unit
1401 Blood pressure measurement device
1402 Blood pressure estimation device
1403 Pressure control unit
20 Computing device
21 CPU
22 Memory
23 Disk
24 Nonvolatile recording medium
25 Input device
26 Output device
27 Communication IF

The invention claimed is:

1. A blood pressure estimation device comprising:
a blood pressure estimation unit configured to estimate a blood pressure on the basis of a pressure in a certain time period and difference between a plurality of pulse wave signals measured in association with the pressure.

2. The blood pressure estimation device according to claim 1, wherein
the blood pressure estimation unit calculates a pulse wave value representing the plurality of pulse wave signals when the plurality of pulse wave signals satisfy a predetermined condition, and estimates the blood pressure on the basis of difference between the pulse wave values calculated for the plurality of pulse wave signals.

3. The blood pressure estimation device according to claim 2, wherein
the pulse wave value is a phase obtained by frequency space transformation of the corresponding pulse wave signal, and
the difference is difference between the phases of the plurality of pulse wave signals.

4. The blood pressure estimation device according to claim 2, wherein
the pulse wave value is an amplitude obtained by frequency space transformation of the corresponding pulse wave signal, and
the difference is a ratio between the amplitudes of the plurality of pulse wave signals.

5. The blood pressure estimation device according to claim 2, wherein
the pulse wave value is a timing at which the corresponding pulse wave signal reaches an extremum or an approximate extremum in a single heartbeat, and
the difference is difference between the timings of the plurality of pulse wave signals.

6. The blood pressure estimation device according to claim 2, wherein
the pulse wave value is an amplitude obtained when the corresponding pulse wave signal reaches an extremum or an approximate extremum in a single heartbeat, and
the difference is a ratio between the amplitudes of the plurality of pulse wave signals.

7. A blood pressure measurement device comprising:
the blood pressure estimation device according to claim 1; and
a pressure control unit configured to control internal pressure of a cuff according to the difference.

8. The blood pressure measurement device according to claim 7, further comprising:
a first pulse wave measurement unit configured to measure a pulse wave at upstream of an artery in the certain time period in association with a certain pressure, and transmit the measured pulse wave as the pulse wave signal to the blood pressure estimation device; and a second pulse wave measurement unit configured to measure the pulse wave at downstream of the artery in the certain time period in association with the certain pressure, and transmit the measured pulse wave as the pulse wave signal to the blood pressure estimation device, wherein the blood pressure estimation device receives the pulse wave signal transmitted by the first pulse wave measurement unit and the pulse wave signal transmitted by the second pulse wave measurement unit, and estimates the blood pressure on the basis of the two received pulse wave signals.

9. A blood pressure estimation method comprising; estimating, by using an information processing device, a blood pressure on the basis of a pressure in a certain time period and difference between a plurality of pulse wave signals measured in association with the pressure in the certain time period.

10. A non-transitory recording medium that records a blood pressure estimation program for causing a computer to implement a blood pressure estimation function for estimating a blood pressure on the basis of a pressure in a certain time period and difference between a plurality of pulse wave signals measured in association with the pressure in the certain time period.

11. The blood pressure estimation device according to claim 1, wherein the blood pressure estimation unit estimates a pressure obtained when the difference is largest or around the largest as a systolic blood pressure.

12. The blood pressure estimation device according to claim 1, wherein the blood pressure estimation unit estimates a pressure that is lower than that obtained when the difference is largest or around the largest and that has the difference smaller than or equal to a predetermined value, as a diastolic blood pressure.

13. The blood pressure measurement device according to claim 8, wherein the first pulse wave measurement unit and the second pulse wave measurement unit are arranged so that a shorter-side direction center or a substantially shorter-side direction center of pressure application in the cuff is located between the first pulse wave measurement unit and the second pulse wave measurement unit.

14. The blood pressure measurement device according to claim 8, wherein the first pulse wave measurement unit or the second pulse wave measurement unit is a vibration sensor that detects vibration.

15. The blood pressure measurement device according to claim 8, wherein the first pulse wave measurement unit or the second pulse wave measurement unit is a photoelectric sensor that detects reflected light obtained when light is applied to a specific region or transmitted light obtained when light is applied to a specific region.

16. The blood pressure measurement device according to claim 8, wherein the first pulse wave measurement unit or the second pulse wave measurement unit is a pressure sensor that measures a pressure.

* * * * *